US011303828B2

(12) United States Patent
Ando et al.

(10) Patent No.: US 11,303,828 B2
(45) Date of Patent: Apr. 12, 2022

(54) IMAGING APPARATUS INCLUDING LIGHT SOURCE THAT EMITS PULSED LIGHT, IMAGE SENSOR, AND CONTROL CIRCUIT

(71) Applicant: Panasonic Intellectual Property Management Co., Ltd., Osaka (JP)

(72) Inventors: Takamasa Ando, Osaka (JP); Tsuguhiro Korenaga, Osaka (JP); Toshiya Fujii, Shiga (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 17/127,699

(22) Filed: Dec. 18, 2020

(65) Prior Publication Data

US 2021/0152755 A1 May 20, 2021

Related U.S. Application Data

(63) Continuation of application No. 16/844,753, filed on Apr. 9, 2020, now Pat. No. 10,911,697, which is a (Continued)

(30) Foreign Application Priority Data

Jun. 17, 2015 (JP) .................................. 2015-122390
Jul. 2, 2015 (JP) .................................. 2015-133892

(51) Int. Cl.
*H04N 5/33* (2006.01)
*A61B 5/026* (2006.01)
(Continued)

(52) U.S. Cl.
CPC ........... *H04N 5/332* (2013.01); *A61B 5/0261* (2013.01); *A61B 5/1455* (2013.01);
(Continued)

(58) Field of Classification Search
None
See application file for complete search history.

(56) References Cited

U.S. PATENT DOCUMENTS

| 5,305,759 A | 4/1994 | Kaneko et al. |
| 2004/0111030 A1 | 6/2004 | Zeman |

(Continued)

FOREIGN PATENT DOCUMENTS

| JP | 4-135551 A | 5/1992 |
| JP | 4-189349 A | 7/1992 |

(Continued)

OTHER PUBLICATIONS

Non-Final Office Action issued in U.S. Appl. No. 15/175,340, dated Jan. 26, 2018.

(Continued)

*Primary Examiner* — Talha M Nawaz
(74) *Attorney, Agent, or Firm* — McDermott Will & Emery LLP

(57) ABSTRACT

An imaging apparatus including a light source that, in operation, emits pulsed light to a measurement target; a diffusion member that is disposed between the light source and the measurement target, and diffuses the pulsed light; an image sensor that includes at least one pixel, the at least one pixel including a photodiode and a charge accumulator that, in operation, accumulates signal charge from the photodiode; and a control circuit that, in operation, controls the image sensor. The control circuit causes the image sensor to start to accumulate the signal charge with the charge accumulator in a falling period of a returned pulsed light which is returned from the measurement target to the image sensor due to the emission of the pulsed light, the falling period being a period from start to end of a decrease of an intensity of the returned pulsed light.

11 Claims, 18 Drawing Sheets

Related U.S. Application Data continuation of application No. 16/410,900, filed on May 13, 2019, now Pat. No. 10,652,482, which is a continuation of application No. 16/131,605, filed on Sep. 14, 2018, now Pat. No. 10,334,188, which is a continuation of application No. 15/175,340, filed on Jun. 7, 2016, now Pat. No. 10,104,315.

(51) Int. Cl.
| | |
|---|---|
| *A61B 5/1455* | (2006.01) |
| *A61B 5/00* | (2006.01) |
| *H04N 5/353* | (2011.01) |
| *H04N 5/355* | (2011.01) |
| *H04N 5/225* | (2006.01) |

(52) U.S. Cl.
CPC ......... *A61B 5/4064* (2013.01); *H04N 5/3532* (2013.01); *H04N 5/3559* (2013.01); *H04N 5/2256* (2013.01); *H04N 5/353* (2013.01); *H04N 2005/2255* (2013.01)

(56) References Cited

U.S. PATENT DOCUMENTS

| | | |
|---|---|---|
| 2004/0215082 A1 | 10/2004 | Chance |
| 2005/0219363 A1* | 10/2005 | Kohler .................... G01J 3/524 348/187 |
| 2005/0219545 A1 | 10/2005 | Chan et al. |
| 2006/0077395 A1 | 4/2006 | Chan et al. |
| 2006/0278240 A1 | 12/2006 | Spillman et al. |
| 2008/0239412 A1 | 10/2008 | Kobayashi |
| 2009/0009595 A1 | 1/2009 | Ishiwata et al. |
| 2009/0023991 A1 | 1/2009 | Gono et al. |
| 2010/0019127 A1 | 1/2010 | Kagawa et al. |
| 2010/0060853 A1* | 3/2010 | Bille .................... A61B 5/0059 351/206 |
| 2010/0201797 A1 | 8/2010 | Shizukuishi et al. |
| 2011/0069199 A1* | 3/2011 | Yamazaki ............ A61B 1/0005 348/229.1 |
| 2011/0172509 A1 | 7/2011 | Chance |
| 2011/0230738 A1 | 9/2011 | Chance |
| 2012/0193692 A1* | 8/2012 | Kawahito ............ H04N 5/3597 257/292 |

FOREIGN PATENT DOCUMENTS

| | | |
|---|---|---|
| JP | 11-164826 A | 6/1999 |
| JP | 2003-010189 A | 1/2003 |
| JP | 2003-534030 A | 11/2003 |
| JP | 2005-283472 A | 10/2005 |
| JP | 2006-112864 A | 4/2006 |
| JP | 2006-314557 A | 11/2006 |
| JP | 2007-260123 A | 10/2007 |
| JP | 2010-194291 A | 9/2010 |
| JP | 2010-232477 A | 10/2010 |
| JP | 2011-013138 A | 1/2011 |
| JP | 2013-224838 A | 10/2013 |

OTHER PUBLICATIONS

Notice of Allowance issued in U.S. Appl. No. 15/175,340 dated Jun. 15, 2018.
Notice of Allowance issued in U.S. Appl. No. 16/131,605 dated Feb. 13, 2019.
Non-Final Office Action dated Sep. 6, 2019 in U.S. Appl. No. 16/410,900.
Notice of Allowance dated Jan. 10, 2020 in U.S. Appl. No. 16/410,900.
Notice of Allowance issued in U.S. Appl. No. 16/844,753, dated Sep. 21, 2020.

* cited by examiner

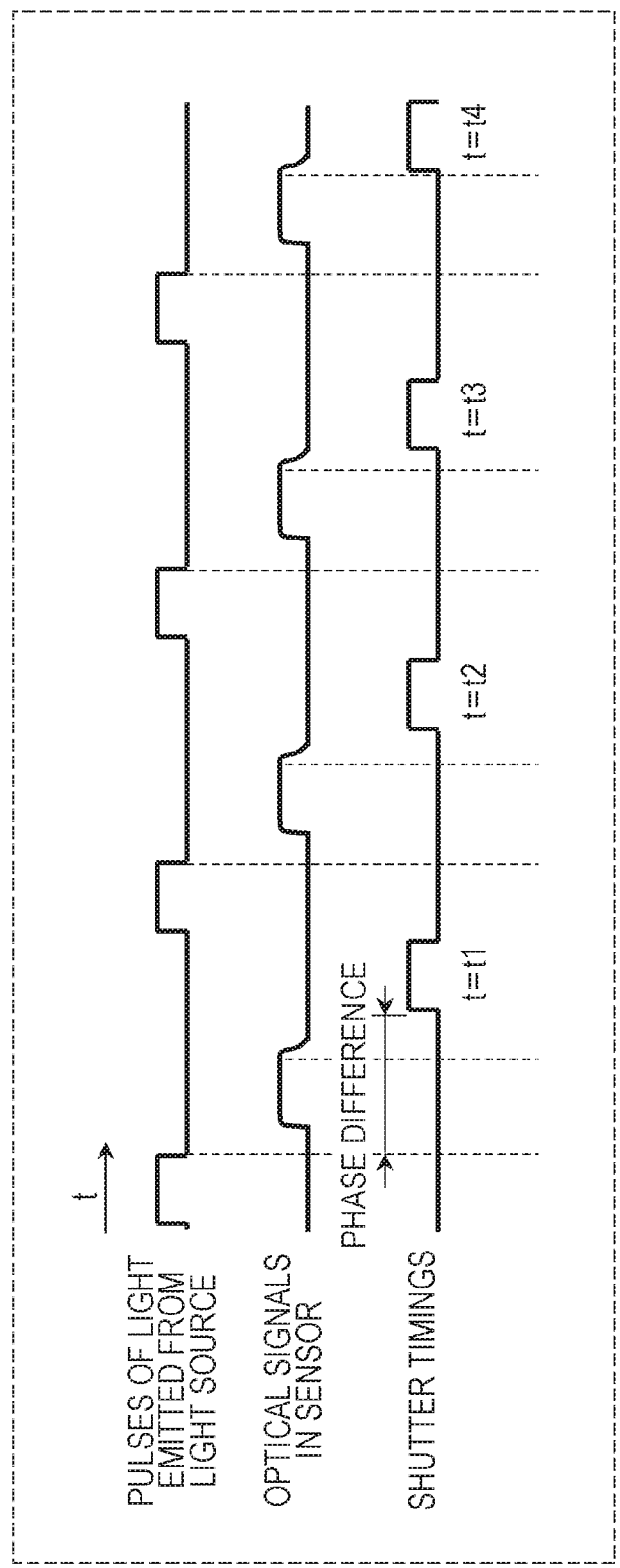

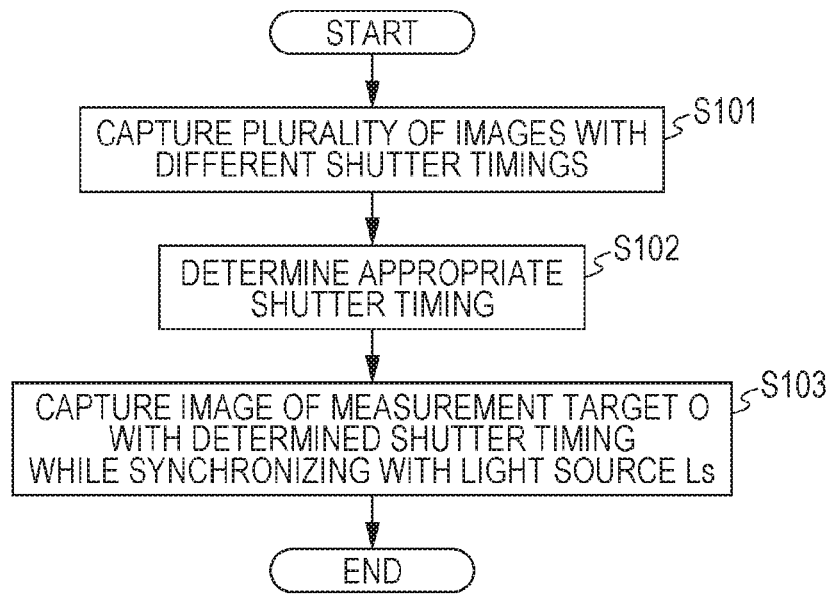
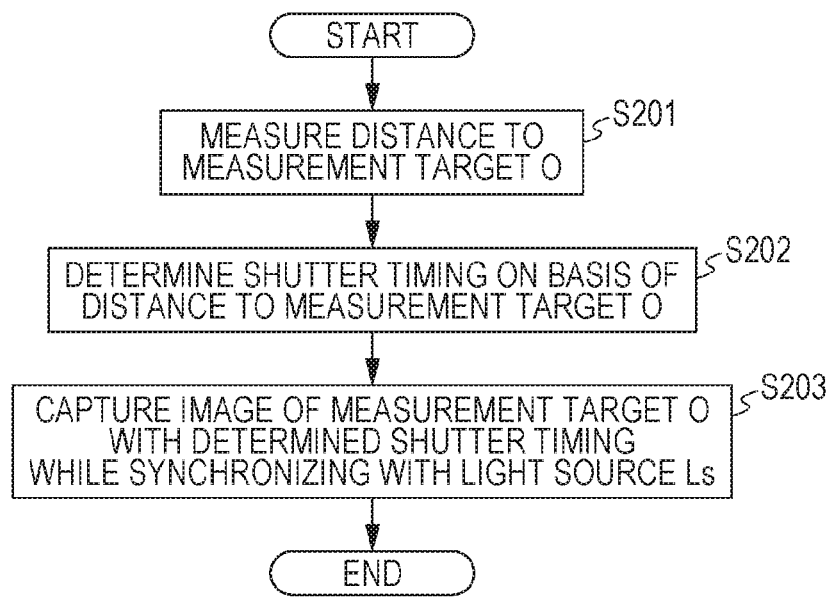

IMAGING APPARATUS INCLUDING LIGHT SOURCE THAT EMITS PULSED LIGHT, IMAGE SENSOR, AND CONTROL CIRCUIT

CROSS-REFERENCE OF RELATED APPLICATIONS

This application is a Continuation of U.S. patent application Ser. No. 16/844,753, filed Apr. 9, 2020, which is a Continuation of U.S. patent application Ser. No. 16/410,900, filed May 13, 2019, now U.S. Pat. No. 10,652,482, which is a Continuation of U.S. patent application Ser. No. 16/131,605, filed on Sep. 14, 2018, now U.S. Pat. No. 10,334,188, which is a Continuation of U.S. patent application Ser. No. 15/175,340, filed on Jun. 7, 2016, now U.S. Pat. No. 10,104,315, which in turn claims the benefit of Japanese Application No. 2015-133892, filed on Jul. 2, 2015 and Japanese Patent Application No. 2015-122390, filed on Jun. 17, 2015, the entire disclosures of which applications are incorporated by reference herein.

BACKGROUND

1. Technical Field

The present disclosure relates to an imaging apparatus.

2. Description of the Related Art

In fields of biometrics and material analyses, methods are used in which light is emitted to a target and internal information regarding the target is obtained on the basis of information regarding the light that has passed through the target. In these methods, components reflected from a surface of the target sometimes act as noise. As a method for removing noise caused by these surface reflection components and obtaining only desired internal information, a method disclosed in Japanese Unexamined Patent Application Publication No. 11-164826, for example, is known in the field of biometrics. In Japanese Unexamined Patent Application Publication No. 11-164826, a method is disclosed in which a light source and a photodetector are attached to a target with the light source and the photodetector separated from each other by a certain distance.

SUMMARY

In one general aspect, the techniques disclosed here feature an imaging apparatus including a light source that, in operation, emits pulsed light to a measurement target; a diffusion member that is disposed between the light source and the measurement target, and diffuses the pulsed light; an image sensor that includes at least one pixel, the at least one pixel including a photodiode and a charge accumulator that, in operation, accumulates signal charge from the photodiode; and a control circuit that, in operation, controls the image sensor, wherein the control circuit, in operation, causes the image sensor to start to accumulate the signal charge with the charge accumulator in a falling period of a returned pulsed light which is returned from the measurement target to the image sensor due to the emission of the pulsed light, the falling period being a period from start to end of a decrease of an intensity of the returned pulsed light.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3B is a diagram illustrating a relationship between the pulsed light emitted from the light source, the optical signal in the image sensor, and the shutter timing according to the second embodiment;

FIG. 4A is a flowchart illustrating an operation performed by an imaging apparatus according to the second embodiment;

FIG. 4B is a flowchart illustrating an operation performed by the imaging apparatus according to an embodiment different from that illustrated in FIG. 4A;

DETAILED DESCRIPTION

Figure 1A:
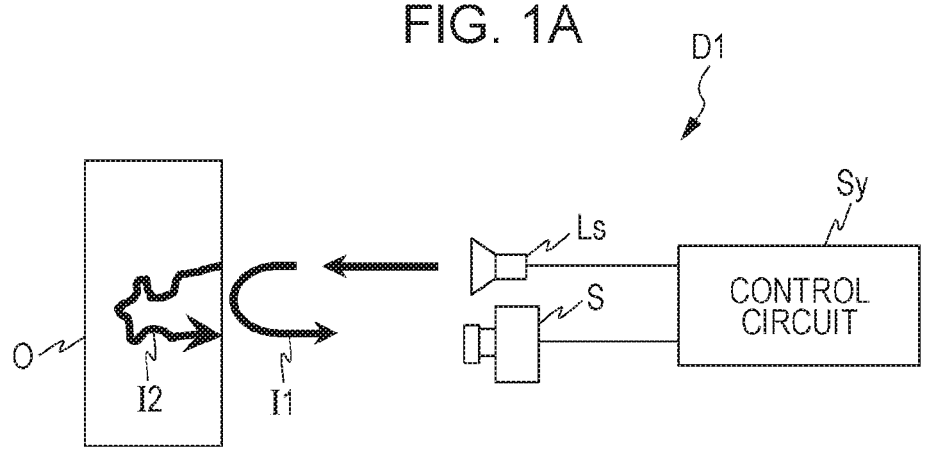
FIG. 1A is a schematic diagram illustrating an imaging apparatus according to a first embodiment and a state in which the imaging apparatus captures an image of a measurement target.

Before describing embodiments of the present disclosure, a result of an examination of a method described in Japanese Unexamined Patent Application Publication No. 4-189349, which is an example of the related art that measures internal information regarding a target in a noncontact manner, will be described hereinafter.

In Japanese Unexamined Patent Application Publication No. 4-189349, information located at different positions in a depth direction in an inside of the target is distinguished from each other through time resolution. Light that has been emitted from a light source and has passed through the target reaches a photodetector later as the light reaches deeper into the target. The information in the depth direction is distinguished on the basis of this time difference. In Japanese Unexamined Patent Application Publication No. 4-189349, ultrashort pulsed light whose pulse width is hundreds of femtoseconds to several picoseconds is emitted to the target in order to perform measurement with a spatial resolution of 2 to 3 mm in the depth direction. In addition, a streak camera having almost the same (about a value obtained by dividing 2 to 3 mm by light speed) temporal resolution detects the light. The streak camera converts the light that has reached a light receiving unit (photoelectric conversion unit) thereof into electrons and sweeps the electrons at high speed in a direction perpendicular to a traveling direction. As a result, spatial displacements occur in accordance with times at which photons have reached the light receiving unit. By detecting these displacements using a two-dimensional fluorescent screen, temporal information can be converted into spatial information.

According to the examination conducted by the present inventors, in the method described in Japanese Unexamined Patent Application Publication No. 4-189349, measurement is performed using a two-dimensional fluorescent screen, but one of the two dimensions is used for the temporal information. That is, the spatial information regarding the target is obtained using only the remaining one dimension. In addition, since an ultrashort pulsed light source whose pulse width is hundreds of femtoseconds to several picoseconds and a streak camera is used, cost is undesirably extremely high.

An imaging apparatus according to a first aspect of the present disclosure includes a light source that, in operation, emits pulsed light to a living body, an image sensor that includes at least one pixel including a photodiode and charge accumulators that, in operation, accumulate signal charge from the photodiode, and a control circuit that, in operation, controls the image sensor, wherein the charge accumulators, in operation, accumulate the signal charge corresponding to a component of the pulsed light scattered inside the living body.

An imaging apparatus according a second aspect of the present disclosure is the imaging apparatus according to the first aspect further including an arithmetic circuit that, in operation, obtains biological information regarding the living body by calculating the signal charge corresponding to the component of the pulsed light scattered inside the living body.

The biological information may be information regarding a cerebral blood flow.

An imaging apparatus according to a third aspect of the present disclosure is the imaging apparatus according to the first or second aspect in which: the image sensor further includes an electronic shutter; the control circuit, in operation, causes the electronic shutter to prevent the charge accumulators from accumulating the signal charge while a part of the pulsed light is reflected from a surface of the living body and reaches the image sensor; and the control circuit, in operation, causes the electronic shutter to allow the charge accumulators to accumulate the signal charge while another part of the pulsed light is scattered inside the living body and reaches the image sensor.

An imaging apparatus according to a fourth aspect of the present disclosure is the imaging apparatus according to any of the first to third aspects in which the at least one pixel comprises pixels arranged in two dimensions.

An imaging apparatus according to a fifth aspect of the present disclosure is the imaging apparatus according to the third aspect in which the control circuit, in operation, causes the electronic shutter to allow the charge accumulators to begin to accumulate the signal charge when a trailing edge of the pulsed light is reflected from the surface of the living body and reaches the image sensor or later.

An imaging apparatus according to a sixth aspect of the present disclosure is the imaging apparatus according to the first or second aspect in which: the control circuit, in operation, causes the charge accumulators to begin to accumulate the signal charge a period of time after the light source begins to emit the pulsed light; and the control circuit, in operation, determines the period of time on the basis of intensity of the signal charge accumulated in the charge accumulators.

An imaging apparatus according to a seventh aspect of the present disclosure is the imaging apparatus according to the first or second aspect in which: the control circuit, in operation, causes the charge accumulators to begin to accumulate the signal charge a period of time after the light source begins to emit the pulsed light; the control circuit, in operation, calculates a distance between the image sensor and the living body; and the control circuit, in operation, determines the period of time on the basis of the distance.

An imaging apparatus according to an eighth aspect of the present disclosure is the imaging apparatus according to any of the first to seventh aspects in which the light source, in operation, emits first pulsed light and second pulsed light in a wavelength band different from a wavelength band of the first pulsed light.

An imaging apparatus according to a ninth aspect of the present disclosure is the imaging apparatus according to any of the first to eighth aspects in which the image sensor is configured to obtain a multi-wavelength image.

An imaging apparatus according to a tenth aspect of the present disclosure is the imaging apparatus according to the first or second aspect in which: the control circuit, in operation, causes the charge accumulators to accumulate the signal charge at a plurality of times when a trailing edge of the pulsed light is reflected from a surface of the living body and reaches the image sensor or later; and the control circuit, in operation, obtains an optical length distribution of the component of the pulsed light scattered inside the living body on the basis of a change in intensity of the signal charge accumulated at the plurality of times.

An imaging apparatus according to an eleventh aspect of the present disclosure is the imaging apparatus according to any of the first to tenth aspects further including a correction circuit that, in operation, corrects movement of the living body.

An imaging apparatus according to a twelfth aspect of the present disclosure is the imaging apparatus according to the eleventh aspect in which the correction circuit, in operation, corrects the movement of the living body by detecting periodic vibration of the living body.

The embodiments that will be described hereinafter are general or specific examples. Values, shapes, materials, components, positions at which the components are arranged, and the like described in the following embodiments are examples, and do not limit the present disclosure. Among the components described in the following embodiments, ones not described in an independent claim, which defines a broadest concept, will be described as arbitrary components.

The embodiments will be specifically described hereinafter with reference to the drawings.

First Embodiment

1. Imaging Apparatus

First, the configuration of an imaging apparatus D1 according to a first embodiment will be described with reference to FIGS. 1A to 2.

FIG. 1A is a schematic diagram illustrating the imaging apparatus D1 according to the present embodiment. The imaging apparatus D1 includes alight source Ls, an image sensor S, and a control circuit Sy.

1-1. Light Source Ls

The light source Ls emits light to a measurement target O. The light that has been emitted from the light source Ls and has reached the measurement target O is divided into a component (surface reflection component I1) reflected from a surface of the measurement target O and a component (internal scattering component I2) reflected or scattered once or scattered multiple times inside the measurement target O. The surface reflection component I1 includes a direct reflection component, a diffuse reflection component, and a scattering reflection component. The direct reflection component is a reflection component whose incident angle and reflection angle are the same. The diffuse reflection component is a component diffusely reflected from uneven portions of the surface. The scattering reflection component is a component scattered by internal tissues near the surface. If the measurement target O is human skin, the scattering reflection component is a component scattered inside epidermis. In the present disclosure, the component (surface reflection component I1) reflected from the surface of the measurement target O will be described as including these three components. The internal scattering component I2 that will be described hereinafter, therefore, does not include the component scattered by the internal tissues near the surface. Traveling directions of the surface reflection component I1 and the internal scattering component I2 change due to reflection or scattering, and part of the surface reflection component I1 and the internal scattering component I2 reaches the image sensor S. The light source Ls generates pulsed light a plurality of times at certain time intervals or at certain timings. A fall time of the pulsed light generated by the light source Ls may be close to zero and, for example, the pulsed light is a rectangular wave. A rise time of the pulsed light generated by the light source Ls may be arbitrarily determined. This is because in measurement in which an imaging apparatus in the present disclosure, which will be described later, is used, a falling edge of pulsed light along a time axis is used, but a rising edge is not used. The light source Ls is, for example, a laser such as a laser diode (LD) whose pulsed light includes a falling edge approximately perpendicular to the time axis (having rapid time response characteristics).

If the measurement target O is a living body, for example, wavelengths achieved by the light source Ls may be set between about 650 nm and about 950 nm. The wavelength range is included in a wavelength range of red light to near-infrared light. The term "light" herein is used not only for visible light but also for infrared light.

In order to measure the measurement target O in a noncontact manner, the imaging apparatus D1 in the present disclosure takes into consideration an effect upon the retina if the measurement target O is a person. For this reason, the imaging apparatus D1 may satisfy Class 1 of a laser safety standard set by each country. In this case, light whose intensity is so low that an accessible emission limit (AEL) falls below 1 mW is emitted to the measurement target O. The light source Ls itself, however, need not satisfy Class 1. Class 1 of the laser safety standard may be satisfied, for example, by providing a diffusion plate, a neutral density (ND) filter, or the like in front of the light source Ls and diffusing or attenuating light.

The conventional streak camera described in Japanese Unexamined Patent Application Publication No. 4-189349 has been used for distinguishing information (e.g., absorption coefficients or scattering coefficients) located at different positions in a depth direction of a living body from each other. In order to perform measurement with a desired spatial resolution, therefore, ultrashort pulsed light whose pulse width is on the order of femtoseconds or picoseconds has been used. On the other hand, the imaging apparatus D1 in the present disclosure is used for distinguishing the internal scattering component I2 from the surface reflection component I1. The pulsed light emitted by the light source Ls, therefore, need not be ultrashort pulsed light, that is, the pulse width may be arbitrarily determined. When light is emitted to the forehead in order to measure a cerebral blood flow, the amount of light of the internal scattering component I2 is extremely smaller than that of the surface reflection component I1, namely one thousandth to one ten-thousandth of that of the surface reflection component I1. Furthermore, if the laser safety standard is taken into consideration, the amount of light that may be emitted becomes small, and it becomes very difficult to detect the internal scattering component I2. The amount of light detected can be increased and a signal-to-noise (SN) ratio can be improved, for example, if the light source Ls generates pulsed light whose pulse width is relatively large.

Figure 1B:
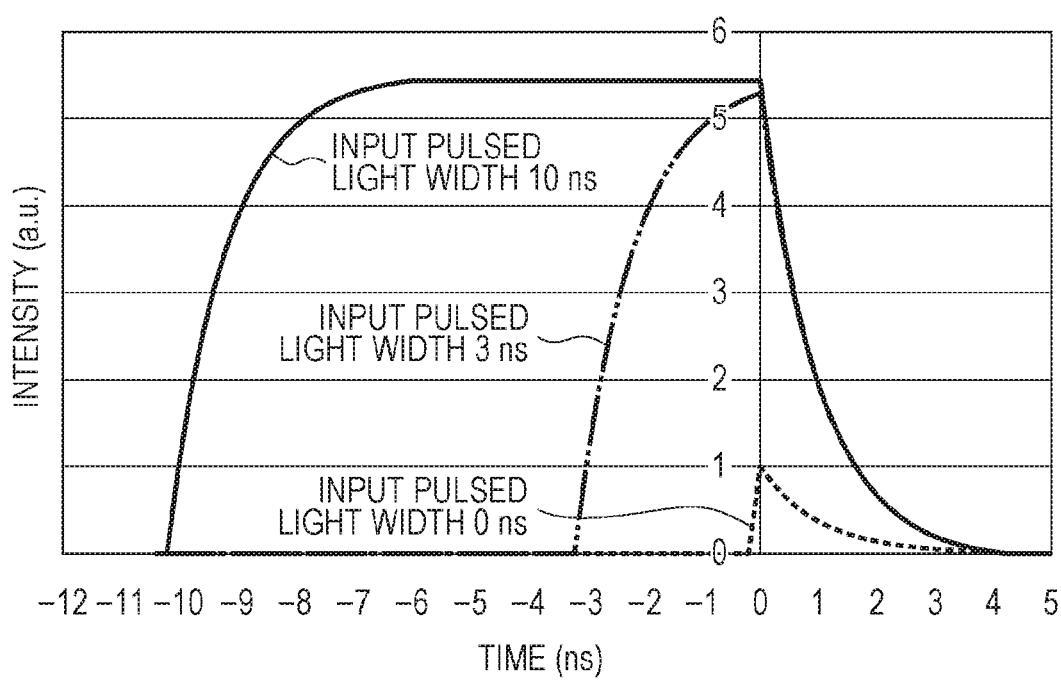
FIG. 1B is a diagram illustrating the pulse width dependence of time characteristics of the amount of light detected by a sensor.
Figure 1C:
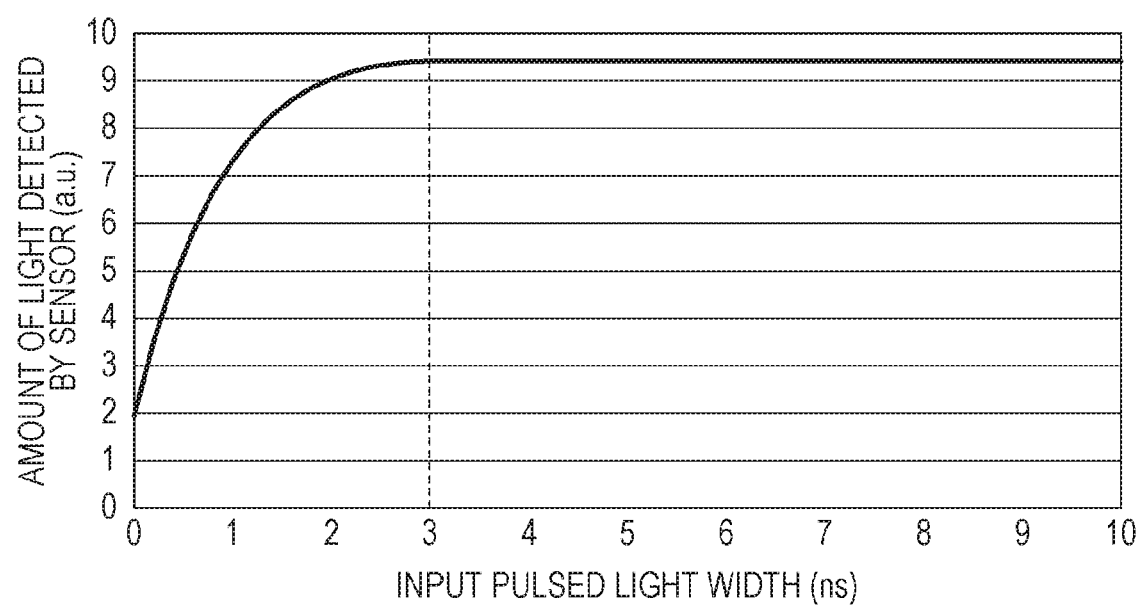
FIG. 1C is a diagram illustrating the pulse width dependence of the amount of light detected by the sensor.

The light source Ls, for example, emits pulsed light having a pulse width of 3 ns or more. The temporal extension of light scattered inside a living body such as a brain is generally about 4 ns. As illustrated in FIG. 1B, therefore, as the width of the pulsed light emitted by the light source Ls increases, the amount of light of the internal scattering component I2 that appears at a trailing edge of the pulsed light returning from the measurement target O increases. FIG. 1C is a diagram in which a horizontal axis represents the width of input pulsed light and a vertical axis represents the amount of light detected by the image sensor S. The image sensor S includes an electronic shutter. Because a ratio of the surface reflection component I1 to the internal scattering component I2 is high immediately after a trailing edge of the pulsed light, the electronic shutter is opened 1 ns after the trailing edge. According to FIG. 1C, when the pulse width of the pulsed light emitted by the light source Ls is 3 ns or more, the amount of light detected by the image sensor S can be maximized.

The light source Ls may emit pulsed light having a pulse width of 5 ns or more, or 10 ns or more. On the other hand, when the pulse width is too large, the amount of light wasted increases. The light source Ls, therefore, generates pulsed light having a pulse width of, for example, 50 ns or less. Alternatively, the light source Ls may emit pulsed light having a pulse width of 30 ns or less, or 20 ns or less.

An emission pattern of the light source Ls may have a uniform intensity distribution, a dotted intensity distribution, or a donut-shaped intensity distribution in an emission area.

1-2. Image Sensor S

The image sensor S receives light emitted from the light source Ls and reflected from the measurement target O. The image sensor S includes a plurality of pixels (light-receiving devices) arranged in two dimensions and obtains two-dimensional information regarding the measurement target O at once. The image sensor S, for example, is a charge-coupled device (CCD) image sensor or a complementary metal-oxide-semiconductor (CMOS) image sensor.

The image sensor S includes an electronic shutter. The electronic shutter is a circuit that controls the length (also referred to as the "shutter width") of a period of one signal accumulation operation in which received light is converted into an effective electrical signal and accumulated, that is, the length of an exposure period (also referred to as an "imaging period"), and a time (referred to as a "shutter timing") taken until an exposure period starts after a previous exposure period ends. In the following description, a state in which the electronic shutter is open (imaging) will be referred to as an "open state", and a state in which the electronic shutter is closed (not imaging) will be referred to as a "closed state". The image sensor S can adjust the shutter timing on the order of sub-nanoseconds, that is, for example, 30 ps to 1 ns, using the electronic shutter. A conventional time-of-flight (ToF) camera intended for distance measurement detects all pulsed light emitted from the light source Ls and reflected from a subject in order to correct the brightness of the subject. The conventional ToF camera, therefore, needs to have a shutter width larger than the pulse width of the pulsed light. On the other hand, the imaging apparatus D1 according to the present embodiment need not correct the amount of light coming from a subject, and the shutter width need not be larger than the pulse width, that is, may be 1 to 30 ns. According to the imaging apparatus D1 according to the present embodiment, since the shutter width is small, dark current included in a detected signal can be reduced.

If the measurement target O is a person's forehead and information such as a cerebral blood flow is to be detected, an attenuation rate of light inside the forehead is extremely high (about one-millionth). When the internal scattering component I2 is detected, therefore, the amount of light might be insufficient with emission of one pulse. In this case, the light source Ls emits pulsed light a plurality of times, and the image sensor S accordingly opens the electronic shutter a plurality of times. Detected signals are integrated with one another to improve sensitivity.

An example of the configuration of the image sensor S will be described hereinafter.

The image sensor S includes a plurality of light detection cells (also referred to as "pixels" herein) arranged on an imaging surface in two dimensions. Each cell includes a light receiving device (e.g., a photodiode).

Figure 1D:
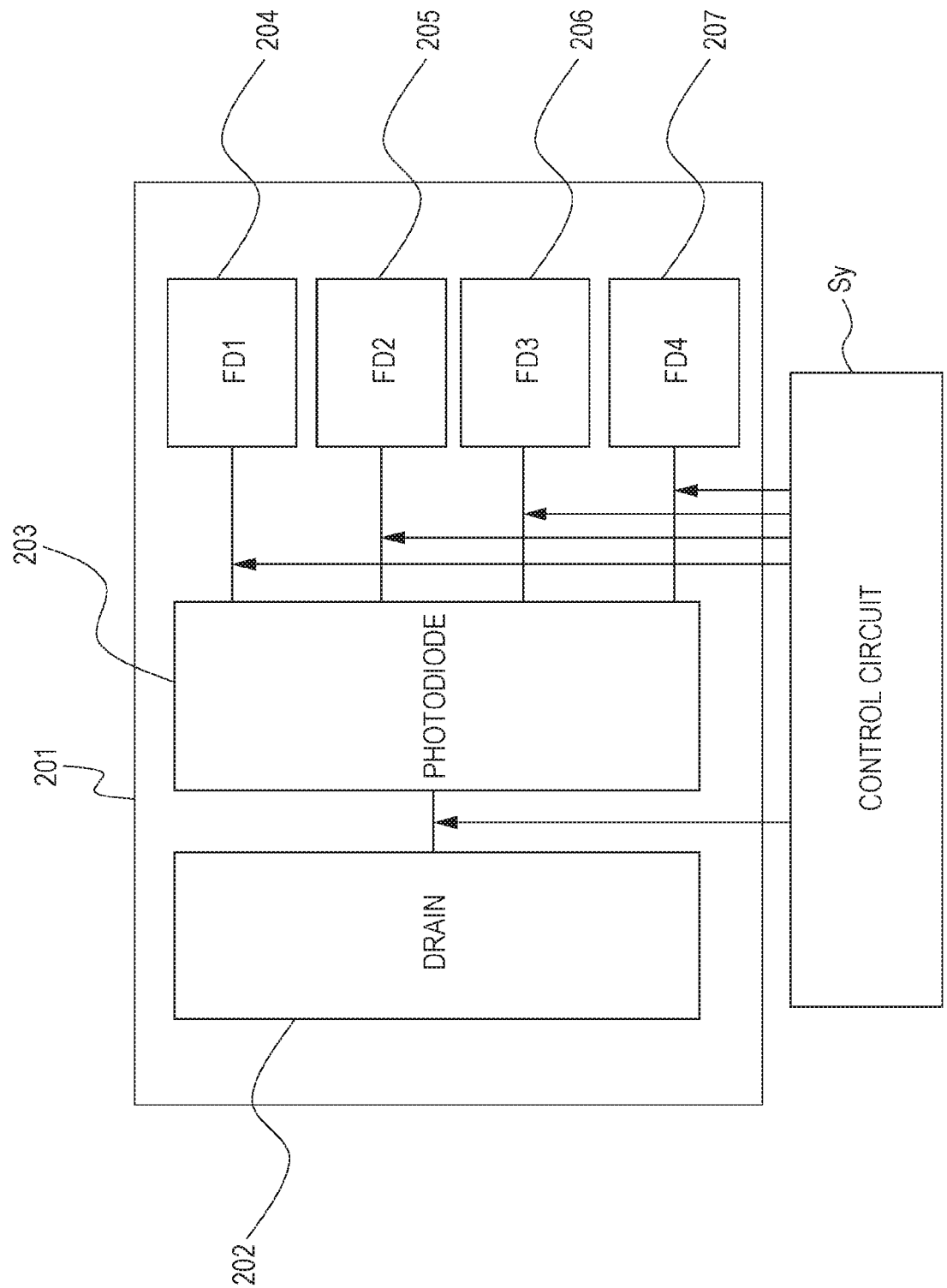
FIG. 1D is a diagram illustrating an example of a schematic configuration of a pixel of an image sensor.

FIG. 1D is a diagram illustrating an example of a schematic configuration of a pixel 201 of the image sensor S. FIG. 1D schematically illustrates the configuration of the pixel 201 and does not necessarily reflect an actual structure. The pixel 201 includes a photodiode 203 that performs photoelectric conversion, first to fourth floating diffusion (FD) layers 204 to 207, which are charge accumulation units that accumulate signal charge, and a drain 202, which is a signal charge discharge unit that discharges signal charge.

Photons that have entered the pixel 201 as a result of emission of one pulse are converted by the photodiode 203 into signal electrons, which are signal charge. The signal electrons obtained as a result of the conversion are discharged to the drain 202 or distributed among the first to fourth FD layers 204 to 207 in accordance with a control signal input from the control circuit Sy.

The emission of pulsed light from the light source Ls, the accumulation of signal charge in the first FD layer (FD1) 204, the second FD layer (FD2) 205, the third FD layer (FD3) 206, and the fourth FD layer (FD4) 207, and the discharge of signal charge to the drain 202 are repeatedly performed in this order. This series of operations is performed at high speed, that is, for example, the series of operations can be performed tens of thousand times to several hundred million times in one frame (e.g., about 1/30 second) of a moving image. The pixel 201 finally generates four image signals based on the signal charge accumulated in the first to fourth FD layers 204 to 207 and outputs the image signals.

The control circuit Sy accumulates signal charge from the photodiode 203 in the first FD layer (FD1) 204 a certain period of time after beginning to emit first pulsed light, and accumulates signal charge from the photodiode 203 in the second FD layer (FD2) 205 the certain period of time after beginning to emit second pulsed light. As a result, accumulation of signal charge starts with a phase of a trailing edge of the first pulsed light and a phase of a trailing edge of the second pulsed light matched with each other in the first FD layer (FD1) 204 and the second FD layer (FD2) 205. If, therefore, a distance to the measurement target O is changed by ±50 cm, for example, the amount of signal charge accumulated increases or decreases in both the first FD layer (FD1) 204 and the second FD layer (FD2) 205. In addition, in order to estimate the amount of disturbance light and ambient light, signal charge may be accumulated in the third FD layer (FD3) 206 with the light source Ls turned off. By subtracting the amount of signal charge in the third FD layer (FD3) 206 from the amount of signal charge in the first FD layer (FD1) 204 or the second FD layer (FD2) 205, a signal from which disturbance light and ambient light components are removed can be obtained. Alternatively, third pulsed light may be accumulated in the fourth FD layer (FD4) 207.

The first pulsed light and the second pulsed light may be light having different wavelengths. By selecting two wavelengths whose absorption rates relative to the measurement target O are different from each other, characteristics of the measurement target O can be analyzed. If light having a wavelength longer than 805 nm is used as the first pulsed light and light having a wavelength shorter than 805 nm is used as the second pulsed light, for example, the amount of change in the concentration of oxyhemoglobin and the amount of change in the concentration of deoxyhemoglobin in a blood flow of the measurement target O can be detected.

Although the number of FD layers is four in the present embodiment, the number of FD layers may be set to two or more in accordance with purposes.

Figure 1E:
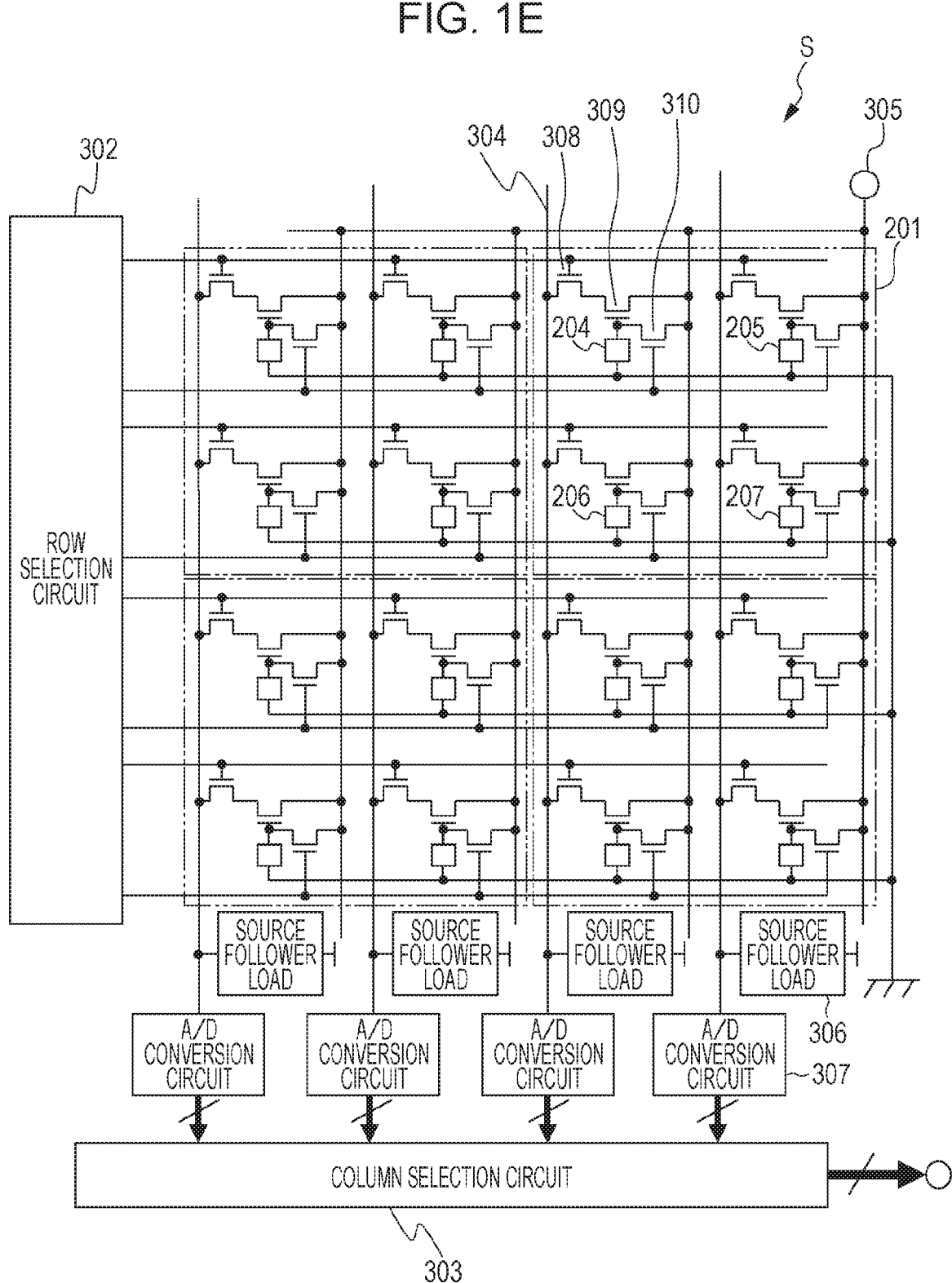
FIG. 1E is a diagram illustrating an example of the configuration of the image sensor.

FIG. 1E is a diagram illustrating an example of the configuration of the image sensor S. In FIG. 1E, each area surrounded by a dash-dot-dot line corresponds to a pixel 201. Although FIG. 1E illustrates only four pixels arranged in two rows and two columns, a larger number of pixels are provided in practice. The pixel 201 includes the first to fourth FD layers 204 to 207. Signals accumulated in the four FD layers 204 to 207 are treated as if the signals are ones in four pixels of a common CMOS image sensor, and output from the image sensor S.

Each pixel 201 includes four signal detection circuits. Each signal detection circuit includes a source follower transistor (amplifying transistor) 309, an FD signal read transistor (row selection transistor) 308, and a reset transistor 310. In this example, the reset transistor 310 corresponds to the drain 202 illustrated in FIG. 1D, and a pulse input to a gate of the reset transistor 310 corresponds to the above-mentioned pulse discharged to the drain 202. Each transistor is a field-effect transistor formed on a semiconductor board, for example, but is not limited to this. As illustrated in FIG. 1E, either an input terminal or an output terminal (typically a source) of the source follower transistor 309 is connected to either an input terminal or an output terminal (typically a drain) of the FD signal read transistor 308. A control terminal (gate) of the source follower transistor 309 is connected to the photodiode 203. Signal charge (holes or electrons) generated by the photodiode 203 is accumulated in the corresponding FD layer, which is a charge accumulation unit, between the photodiode 203 and the source follower transistor 309.

Although not illustrated in FIG. 1E, each of the first to fourth FD layers 204 to 207 is connected to the photodiode 203, and a switch can be provided between the photodiode 203 and each of the first to fourth FD layers 204 to 207. This switch connects or disconnects the photodiode 203 and each of the first to fourth FD layers 204 to 207 in accordance with a signal accumulation pulse from the control circuit Sy. As a result, signal change starts to be accumulated or stops being accumulated in each of the first to fourth FD layers 204 to 207. The electronic shutter in the present embodiment includes a mechanism for performing such exposure control.

The signal charge accumulated in the first to fourth FD layers 204 to 207 is read when a row selection circuit 302 turns on gates of the row selection transistors 308. At this time, current flowing from a source follower power supply 305 to the source follower transistors 309 and source follower loads 306 is amplified in accordance with signal potentials of the first to fourth FD layers 204 to 207. Analog signals caused by the current and read by vertical signal lines 304 are converted into digital signal data by analog-to-digital (A/D) conversion circuits 307, each of which is connected to a corresponding column. The digital signal data is read by a column selection circuit 303 for each column and output from the image sensor S. After reading one row, the row selection circuit 302 and the column selection circuit 303 read a next row, and then sequentially read information regarding signal charge accumulated in the first to fourth FD layers 204 to 207 in all the rows. After reading all the signal charge, the control circuit Sy turns on the gates of the reset transistors 310 to reset all the first to fourth FD layers 204 to 207. Imaging of one frame is thus completed. Similarly, the image sensor S repeats high-speed imaging of a frame in order to complete imaging of a series of frames.

Although the CMOS image sensor S has been taken as an example in the present embodiment, the imaging device used may be a CCD, a single photon counting device, or an amplifying image sensor (electron-multiplying CCD (EMCCD) or intensified CCD (ICCD)), instead.

Figure 1F:
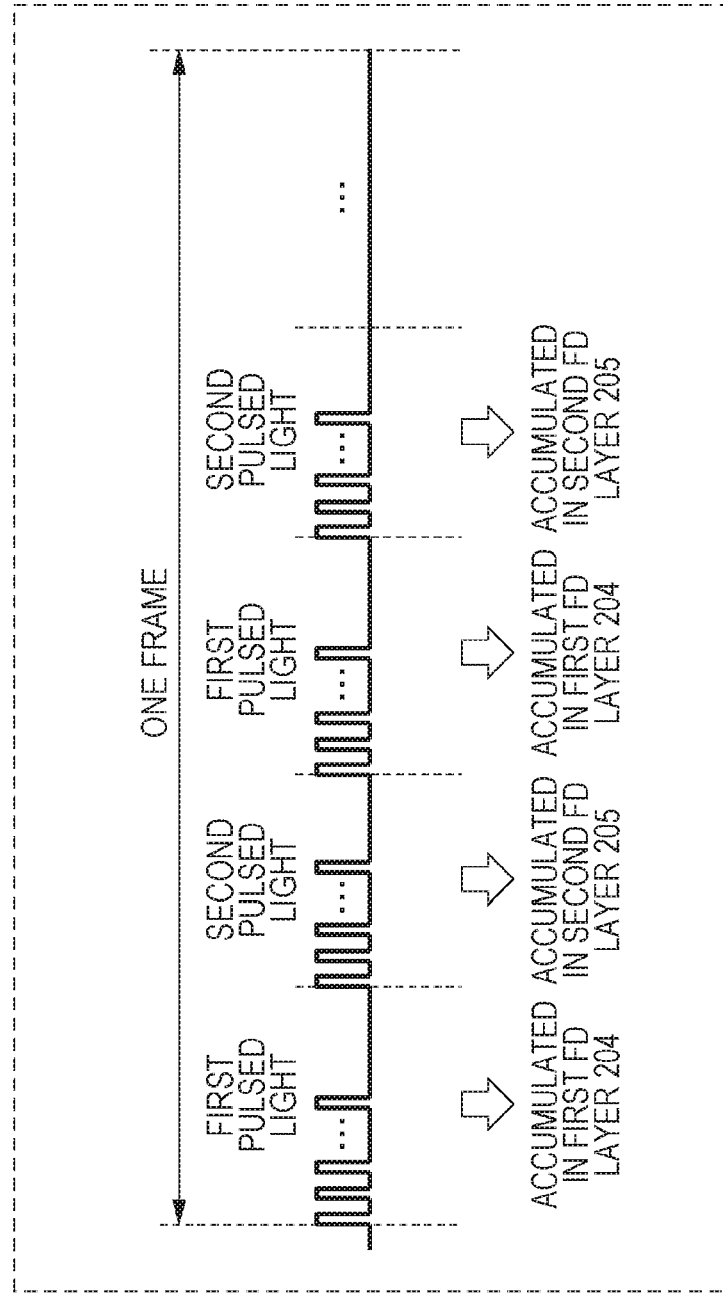
FIG. 1F is a diagram illustrating emission of first pulsed light and second pulsed light in one frame.

As illustrated in FIG. 1F, in the present embodiment, emission of the first pulsed light and emission of the second pulsed light may alternate a plurality of times in a frame. In doing so, a difference between timings at which two types of images are obtained can be reduced, and imaging can be almost simultaneously performed with the first and second pulsed light even for a moving measurement target O.

1-3. Control Circuit Sy

The control circuit Sy adjusts a difference between a timing at which the light source Ls emits pulsed light and a shutter timing of the image sensor S. The difference will also be referred to as a "phase" or a "phase delay" hereinafter. The timing at which the light source Ls emits pulsed light is a timing at which the pulsed light emitted by the light source Ls begins to rise. The control circuit Sy may adjust the phase by changing the timing at which the light source Ls emits pulsed light or by changing the shutter timing.

The control circuit Sy may be configured to remove an offset component from a signal detected by a light-receiving device of the image sensor S. The offset component is a signal component caused by ambient light or disturbance light such as sunlight or light from a fluorescent lamp. If the image sensor S detects a signal with the light source Ls not emitting light, that is, with the light source Ls turned off, the offset component caused by ambient light and disturbance light can be estimated.

The control circuit Sy, for example, can be an integrated circuit including a processor such as a central processing unit (CPU) or a microcomputer and a memory. The control circuit Sy adjusts the timing at which the light source Ls emits pulsed light and the shutter timing, estimates the offset component, and removes the offset timing, for example, by executing programs stored in the memory. The control circuit Sy may further include an arithmetic circuit that performs arithmetic processing such as image processing. Such an arithmetic circuit is achieved, for example, by a combination of a digital signal processor (DSP), a programmable logic device (PLD) such as a field-programmable gate array (FPGA), or a combination of a CPU or a graphics processing unit (GPU) and computer programs. The control circuit Sy and the arithmetic circuit may be integrated as a single circuit, or may be separate circuits.

Figure 1G:
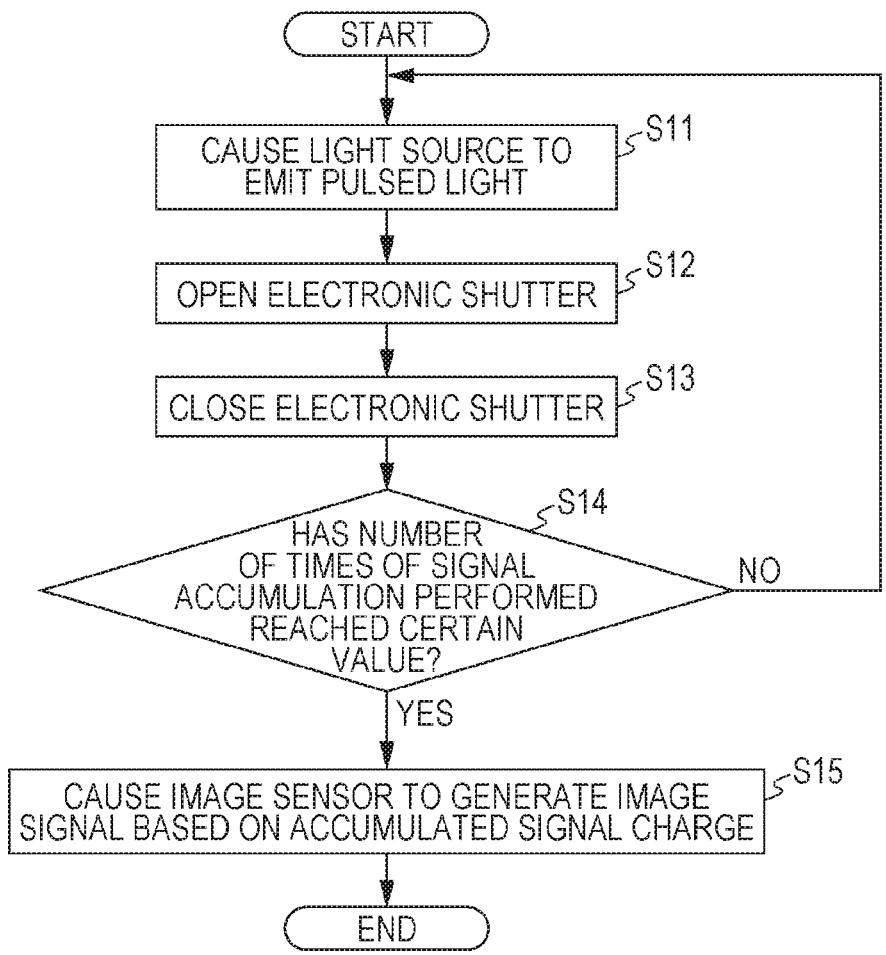
FIG. 1G is a flowchart schematically illustrating an operation performed by a control circuit.

FIG. 1G is a flowchart schematically illustrating an operation performed by the control circuit Sy. Schematically, the control circuit Sy performs the operation illustrated in FIG. 1G, details of which will be described later. First, the control circuit Sy causes the light source Ls to emit pulsed light for a certain period of time (step S11). At this time, the electronic shutter of the image sensor S is closed. The control circuit Sy keeps the electronic shutter closed until a part of the pulsed light is reflected from the surface of the measurement target O and reaches the image sensor S. Next, the control circuit Sy opens the electronic shutter when another part of the pulsed light is scattered inside the measurement target O and reaches the image sensor S (step S12). A certain period of time later, the control circuit Sy closes the electronic shutter (step S13). Next, the control circuit Sy determines whether the number of times of signal accumulation performed has reached a certain value (step S14). If not, the control circuit Sy repeats steps S11 to S13 until the number of times of signal accumulation performed reaches the certain value. If determining in step S14 that the number of times of signal accumulation performed has reached the certain value, the control circuit Sy causes the image sensor S to generate a signal indicating an image based on signal charge accumulated in the FD layers 204 to 207 and output the signal (step S15).

As a result of the above operation, a component of light scattered inside the measurement target O can be sensitively detected. The emission of pulsed light and the exposure by the electronic shutter need not necessarily be performed a plurality of times, but may be performed as necessary.

1-4. Modifications

The imaging apparatus D1 may include an imaging optical system that forms a two-dimensional image of the measurement target O on a light receiving surface of the image sensor S. An optical axis of the imaging optical system is substantially perpendicular to the light receiving surface of the image sensor S. The imaging optical system may include a zoom lens. If a position of the zoom lens changes, the two-dimensional image of the measurement target O is magnified or reduced, and the resolution of the two-dimensional image on the image sensor S changes. Even if the measurement target O is distant, therefore, a desired area can be magnified and closely observed.

In addition, the imaging apparatus D1 may include, between the measurement target O and the image sensor S, a bandpass filter that passes only light in and around a wavelength band of the light emitted from the light source Ls. In this case, an effect of a disturbance component such as ambient light can be reduced. The bandpass filter is a multi-layer film filter or an absorption filter. In consideration of a shift of the band due to the temperature of the light source Ls and oblique incident on the bandpass filter, the bandwidth of the bandpass filter may be 20 to 100 nm.

In addition, the imaging apparatus D1 may include polarizing plates between the light source Ls and the measurement target O and between the image sensor S and the measurement target O. In this case, a polarizing direction of the polarizing plate for the light source Ls and that of the polarizing plate for the image sensor S are crossed Nicols. As a result, it is possible to prevent a regular reflection component (a component whose incident angle and reflection angle are the same) in the surface reflection component I1 of the measurement target O from reaching the image sensor S. That is, the amount of light of the surface reflection component I1 that reaches the image sensor S can be reduced.

2. Operation

The imaging apparatus D1 in the present disclosure distinguishes the internal scattering component I2 from the surface reflection component I1. If the measurement target O is a person's forehead, the signal strength of the internal scattering component I2 to be detected is extremely low. This is because, as described above, an extremely small amount of light that satisfies the laser safety standard is emitted and most of the light is scattered or absorbed by the scalp, cerebral fluid, gray matter, white matter, and blood flow. Furthermore, a change in signal strength due to a change in the volume of blood flow or components in the blood flow while the brain is active is one several tenth of the total signal strength, that is, extremely small. Imaging is therefore performed while eliminating the surface reflection component I1, which is several thousand to several ten thousand times larger than the signal component to be detected, as much as possible.

The operation of the imaging apparatus D1 according to the present embodiment will be described hereinafter.

As illustrated in FIG. 1A, when the light source Ls emits pulsed light to the measurement target O, the surface reflection component I1 and the internal scattering component I2 are caused. Part of the surface reflection component I1 and the internal scattering component I2 reaches the image sensor S. Since, after being emitted from the light source Ls, the internal scattering component I2 passes through the measurement target O before reaching the image sensor S, an optical path of the internal scattering component I2 is longer than that of the surface reflection component I1. The internal scattering component I2, therefore, takes more time to reach the image sensor S than the surface reflection component I1. FIG. 2 is a diagram illustrating optical signals that reach the image sensor S after the light source Ls emits rectangular pulsed light and the measurement target O reflects the pulsed light. A horizontal axis represents time (t) in (a) to (d) of FIG. 2, and a vertical axis represents intensity in (a) to (c) of FIG. 2 and the open or closed state of the electronic shutter in (d) of FIG. 2. The surface reflection component I1 is illustrated in (a) of FIG. 2. The internal scattering component I2 is illustrated in (b) of FIG. 2. A combined component of the surface reflection component I1 illustrated in (a) of FIG. 2 and the internal scattering component I2 illustrated in (b) of FIG. 2 is illustrated in (c) of FIG. 2. As illustrated in (a) of FIG. 2, the surface reflection component I1 is rectangular. On the other hand, as illustrated in (b) of FIG. 2, since the internal scattering component I2 is a combination of light beams that have passed along various optical paths, the internal scattering component I2 has a "tail" at a trailing edge of the pulsed light (a fall time is longer than that of the surface reflection component I1). In order to extract the internal scattering component I2 from the optical signal illustrated in (c) of FIG. 2, the electronic shutter is opened after a trailing edge of the surface reflection component I1 (when or after the surface reflection component I1 falls) as illustrated in (d) of FIG. 2. This shutter timing is adjusted by the control circuit Sy. As illustrated above, since it is only required that the imaging apparatus D1 in the present disclosure be able to distinguish the internal scattering component I2 from the surface reflection component I1, the pulse width and the shutter width may be arbitrarily determined. As a result, unlike the method in an example of the related art in which a streak camera is used, the imaging apparatus D1 in the present disclosure can be achieved with a simple configuration, and cost can be significantly reduced.

If the measurement target O does not have a flat surface, a time at which light reaches is different between the pixels of the image sensor S. In this case, the shutter timing illustrated in (d) of FIG. 2 may be determined in accordance with pixels corresponding to a target area of the measurement target O. Alternatively, depth information regarding a surface of the measurement target O may be detected in advance by a known method, and the shutter timing may be changed for each pixel on the basis of the depth information. The depth information is positional information in a z direction when a direction of the optical axis of the imaging optical system is denoted by z. An optimal shutter timing for extracting the internal scattering component I2 can thus be set at each position in accordance with curves of the surface of the measurement target O.

Figure 2:
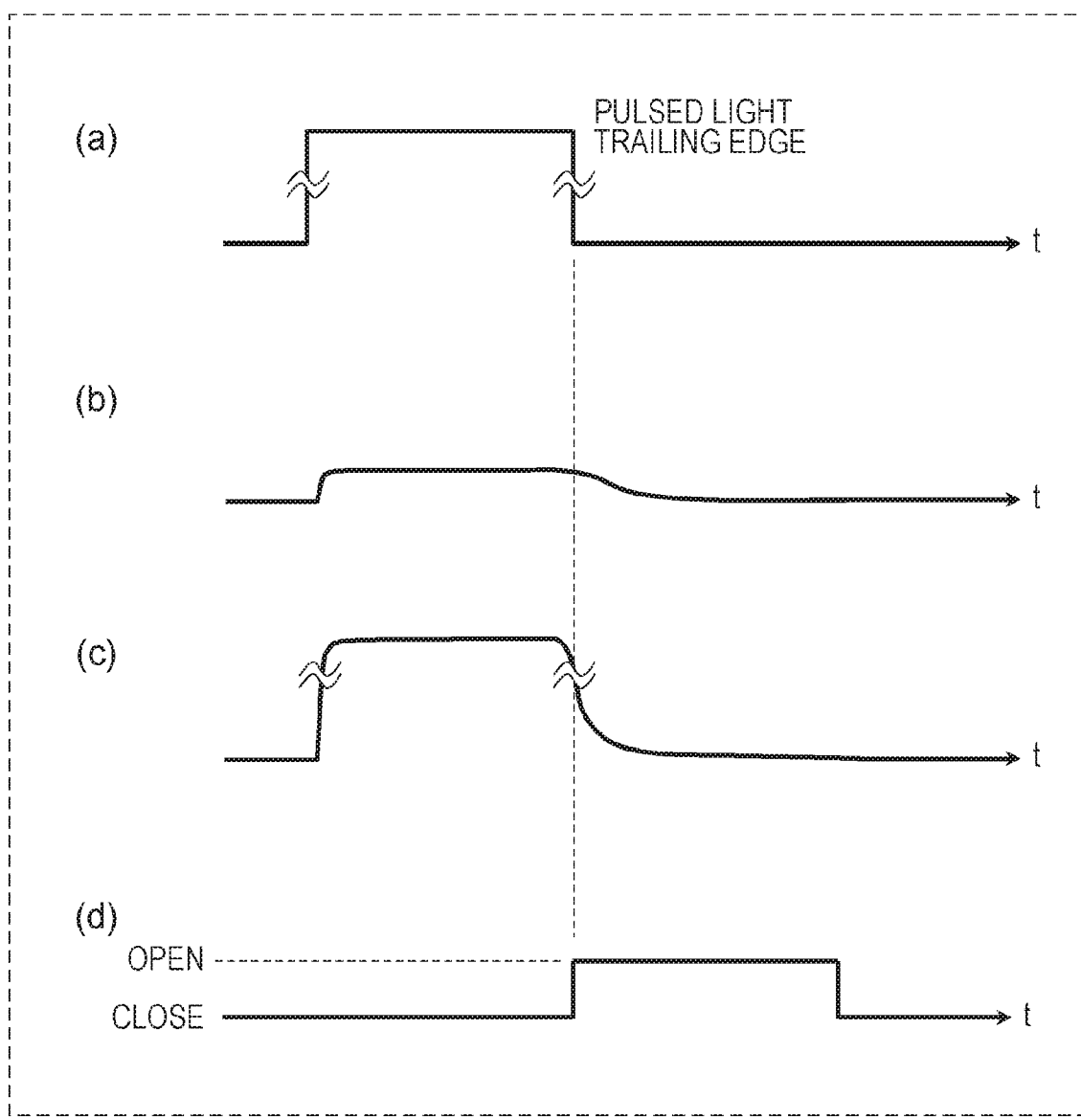
FIG. 2 is a diagram illustrating optical signals caused by rectangular pulsed light that has been emitted from a light source, reflected from the measurement target, and has reached the image sensor.

In (a) of FIG. 2, the trailing edge of the surface reflection component I1 falls vertically. In other words, a time taken for the surface reflection component I1 to finish falling is zero. In practice, however, the pulsed light emitted by the light source Ls might not be perfectly vertical, or the surface of the measurement target O might be slightly uneven. In this case, the trailing edge of the surface reflection component I1 might not fall vertically. In addition, because the measurement target O is usually opaque, the amount of light of the surface reflection component I1 is significantly larger than that of the internal scattering component I2. Even if the trailing edge of the surface reflection component I1 only slightly fails to fall vertically, therefore, the internal scattering component I2 undesirably gets buried in the surface reflection component I1. In addition, ideal binary reading illustrated in (d) of FIG. 2 might not be achieved due to a delay according to movement of electrons during a reading period of the electronic shutter. The control circuit Sy, therefore, may delay the shutter timing of the electronic shutter from a point in time immediately after the fall of the surface reflection component I1. The control circuit Sy, for example, may delay the shutter timing by 0.5 to 5 ns. In addition, in order to obtain only information regarding portions deeper than a desired depth of the measurement target O, the control circuit Sy may further delay the shutter timing of the electronic shutter. Instead of adjusting the shutter timing of the electronic shutter, the control circuit Sy may adjust the timing at which the light source Ls emits pulsed light. The control circuit Sy may adjust a difference between the shutter timing of the electronic shutter and the timing at which the light source Ls emits pulsed light. When a change in the volume of the blood flow or the components in the blood flow while the brain is active is measured in a noncontact manner, the internal scattering component I2 undesirably further decreases if the shutter timing is too late. The shutter timing, therefore, may stay around the trailing edge of the surface reflection component I1.

The light source Ls may emit pulsed light a plurality of times and the electronic shutter may be opened a plurality of timings such that the same phase is maintained for the pulsed light, in order to amplify the amount of light of the internal scattering component I2 detected.

Instead of, or in addition to, providing a bandpass filter between the measurement target O and the image sensor S, the control circuit Sy may perform imaging with the light source Ls turned off and the exposure period remaining the same in order to estimate the offset component. The estimated offset component is differentially removed from signals detected by the light receiving devices of the image sensor S. A dark current component caused in the image sensor S can thus be removed.

As described above, in the imaging apparatus D1 in the present disclosure, the control circuit Sy causes the light source Ls to emit pulsed light and closes the electronic shutter in a period in which a part of the pulsed light is reflected from the surface of the measurement target O and reaches the image sensor S. On the other hand, the control circuit Sy opens the electronic shutter in a period in which another part of the pulsed light is scattered inside the measurement target O and reaches the image sensor S. As a result, internal information regarding the measurement target O can be obtained while suppressing noise caused by a component reflected from the surface. A time at which the electronic shutter is opened may be a time at which a trailing edge of the pulsed light reflected from the surface of the measurement target O reaches the image sensor S or later. The internal information regarding the measurement target O can thus be obtained almost without the noise caused by the component reflected from the surface.

Second Embodiment

A second embodiment is different from the first embodiment in that the control circuit Sy determines a phase of a shutter timing. Detailed description of features common to the second embodiment and the first embodiment is omitted herein.

Figure 3A:
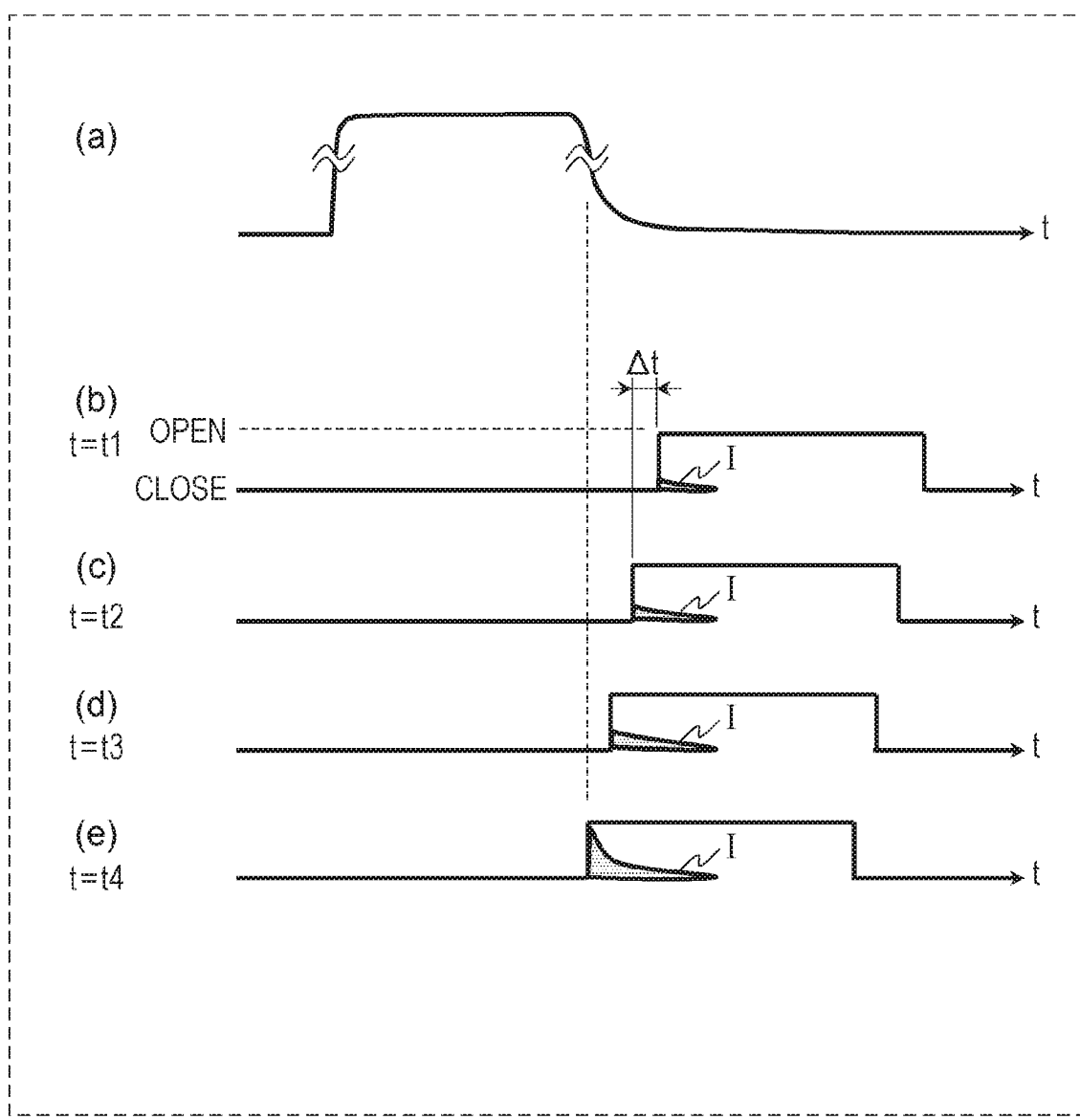
FIG. 3A is a diagram illustrating a relationship between an optical signal in the image sensor, a shutter timing, and a detected optical signal according to a second embodiment.

A time taken until light emitted from the light source Ls returns to the image sensor S after being reflected from the measurement target O depends on a traveling distance of the light. The phase of a shutter timing, therefore, is adjusted in accordance with a distance between the imaging apparatus D1 and the measurement target O. FIG. 3A is a diagram illustrating an example of the adjustment of a shutter timing. A time response waveform of an optical signal that reaches the image sensor S is illustrated in (a) of FIG. 3A. The optical signal illustrated in (a) of FIG. 3A is a signal including both the surface reflection component I1 and the internal scattering component I2. A shutter timing (t=t1) sufficiently later than a time at which the optical signal illustrated in (a) of FIG. 3A begins to fall is illustrated in (b) of FIG. 3A. If the light source Ls emits pulsed light a plurality of times, a phase t between the fall of the optical signal illustrated in (a) of FIG. 3A and a next rise of the optical signal is set. At this time, an optical signal from the measurement target O is not detected at all, or only a small optical signal I at a trailing edge is detected. This optical signal I has a relatively long optical path, that is, includes a relatively large amount of information regarding a deeper portion of the measurement target O. A shutter timing (t=t2) earlier than that illustrated in (b) of FIG. 3A by a time Δt is illustrated in (c) of FIG. 3A. In this case, the amount of light of the optical signal I detected increases in accordance with the advance in the shutter timing. Shutter timings (t=t3 and t=t4, respectively, and t3>t4) even earlier than that illustrated in (c) of FIG. 3A are illustrated in (d) and (e) of FIG. 3A. The shutter timing is thus gradually advanced. A point in time at which the optical signal I detected by the image sensor S begins to increase sharply corresponds to a trailing edge of the surface reflection component I1. If the shutter timing comes immediately before the sharp increase, therefore, a signal mainly composed of the internal scattering component I2 can be detected. The time Δt, by which the shutter timing is advanced, is shorter than an extension (fall time) of a trailing edge of the internal scattering component I2. The time Δt, for example, is 30 ps to 1 ns. FIG. 3B illustrates a relationship between pulses of light emitted from the light source Ls, optical signals that reach the image sensor S, and shutter timings. The light source Ls is periodically emitting pulsed light. Although the light source Ls emits pulsed light after the shutter closes, a period for which the shutter remains open and a period for which the light source Ls emits pulsed light may overlap with each other. An off period between two consecutive beams of pulsed light emitted from the light source Ls, for example, may be up to four times as long as the shutter width, twice as long as the shutter width, or 1.5 times as long as the shutter width. The off period refers to a time taken until pulsed light emitted from the light source Ls rises after the pulsed light finishes falling. The off period may be up to four times as long as the pulse width of the pulsed light emitted from the light source Ls, twice as long as the pulse width, or 1.5 times as long as the pulse width. Since, in this case, the image sensor S can be exposed to more light in unit time, sensitivity improves with a frame rate remaining the same. The off period is too short to be employed in a conventional ToF camera because erroneous detection can occur during distance measurement.

Methods for finding an optimal phase of the shutter timing include iterative methods such as a bisection algorithm and a Newton's method and other numerical calculations, in addition to the method illustrated in FIG. 3A, in which the phase is gradually changed. By one of these methods, the number of times of image capture can be decreased, thereby reducing a time taken to find an appropriate phase.

Alternatively, the phase of the shutter timing may be determined after directly measuring the distance to the measurement target O through triangulation with a binocular or multiocular camera or measurement of a flight time by a ToF method. A time taken for a trailing edge of the surface reflection component I1 of pulsed light emitted from the light source Ls to reach the image sensor S after the light source Ls emits the pulsed light can be estimated on the basis of the measured distance. The control circuit Sy may open the shutter when or after the estimated time elapses. In this case, the control circuit Sy includes an arithmetic circuit that calculates the distance between the imaging apparatus D1 and the measurement target O or a value that depends on the distance.

FIG. 4A is a flowchart illustrating the operation of the imaging apparatus D1 according to the present embodiment. The operation of the imaging apparatus D1 is achieved, for example, when the control circuit Sy controls the components by executing a program stored in the memory.

First, the control circuit Sy controls the phase of the shutter timing and captures a plurality of images. The plurality of images are captured with different phases of the shutter timing (step S101). That is, the control circuit Sy captures the plurality of images with varying differences between the timing at which the light source Ls emits pulsed light and the shutter timing of the image sensor S.

Next, the control circuit Sy determines, for example, whether a change rate of the strength of detected signals obtained from the plurality of images captured in step S101 has exceeded a certain threshold on the basis of changes in the strength over time. If determining that the change rate has exceeded the certain threshold, the control circuit Sy determines an appropriate phase of the shutter timing for subsequent shutter timings (step S102). The appropriate phase, for example, may be a timing at which the threshold is exceeded, or may be a timing later than the foregoing timing by a certain period of time.

Next, the control circuit Sy captures an image of the measurement target O with the phase of the shutter timing determined in step S102 (step S103). That is, the control circuit Sy captures an image of the measurement target O while synchronizing the timing at which the light source Ls emits pulsed light and the shutter timing with each other with the determined time difference. As a result, the imaging apparatus D1 can detect an optical signal mainly composed of the internal scattering component I2. The pulse width of the light source Ls and the shutter width used in step S101 may be the same as or different from ones used in step S103. FIG. 4B is a flowchart illustrating the operation of the imaging apparatus D1 according to an embodiment different from that illustrated in FIG. 4A.

First, the control circuit Sy measures a distance between the imaging apparatus D1 and the image sensor S (step S201). More specifically, the control circuit Sy measures the distance to the measurement target O through measurement of a flight time by a conventional ToF method or using a multiocular camera that can be included in the imaging apparatus D1.

Next, the control circuit Sy determines the phase of the shutter timing on the basis of the distance measured in step S201 (step S202).

Next, the control circuit Sy captures an image of the measurement target O with the phase of the shutter timing determined in step S202 (step S203). That is, the control circuit Sy captures an image of the measurement target O while synchronizing the timing at which the light source Ls emits pulsed light and the shutter timing with each other with the determined time difference. As a result, the imaging apparatus D1 can detect an optical signal mainly composed of the internal scattering component I2.

Step S101 or S201, for example, may be performed if a user issues a corresponding instruction or if the measurement target O, namely, for example, a head, is detected in an imaging area.

As described above, the control circuit Sy determines the difference between the timing at which the light source Ls begins to emit pulsed light and the timing at which the electronic shutter opens. More specifically, in an example, the control circuit Sy captures a plurality of images with varying differences between the timing at which the light source Ls begins to emit pulsed light and the timing at which the electronic shutter opens. The control circuit Sy then determines the time difference on the basis of the strength of an electrical signal generated by the image sensor S on the basis of the plurality of images. In another example, the control circuit Sy calculates the distance between the image sensor S and the measurement target O and determines the time difference on the basis of the calculated distance. As a result, a shutter timing with which a component reflected from the surface of the measurement target O is hardly detected by the image sensor S can be achieved.

Third Embodiment

A third embodiment is different from the first embodiment in that an imaging apparatus D2 includes a plurality of light sources Ls. Detailed description of features common to the present embodiment and the first embodiment is omitted herein.

Figure 5:
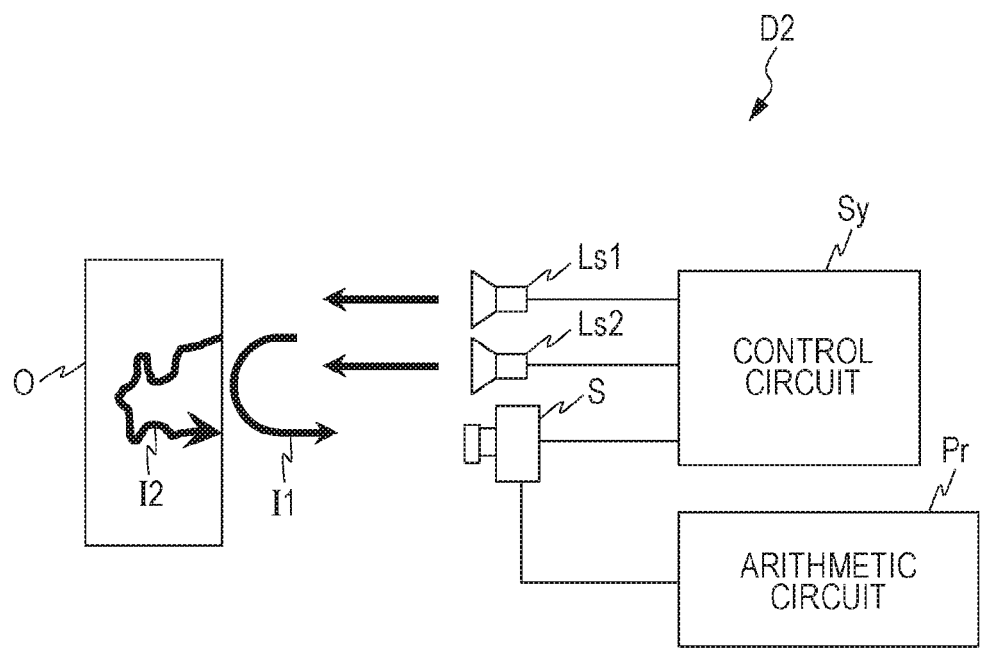
FIG. 5 is a schematic diagram illustrating an imaging apparatus according to a third embodiment and a state in which the imaging apparatus captures the measurement target.

FIG. 5 is a schematic diagram illustrating the imaging apparatus D2 according to the third embodiment. The imaging apparatus D2 includes light sources Ls1 and Ls2. The imaging apparatus D2 also includes an arithmetic circuit Pr.

The light sources Ls1 and Ls2 emit light in different wavelength bands. Absorption and scattering characteristics of the measurement target O generally vary depending on the wavelength, components of the measurement target O can be analyzed in more detail by detecting the wavelength dependence of an optical signal caused by the internal scattering component I2. When the measurement target O is a biological tissue, for example, oxyhemoglobin ($HbO_2$) absorbs more light than deoxyhemoglobin (Hb) at a wavelength of 800 nm or higher. On the other hand, an opposite phenomenon occurs at a wavelength shorter than 800 nm. It is assumed, for example, that the light source Ls1 emits light of a wavelength of about 750 nm and the light source Ls2 emits light of a wavelength of about 850 nm. In this case, changes in the concentration of $HbO_2$ and Hb in a blood flow from initial values can be obtained by measuring the light intensity of the internal scattering component I2 caused by the light from the light source Ls1 and the light intensity of the internal scattering component I2 caused by the light from the light source Ls2 and solving resultant simultaneous equations.

The arithmetic circuit Pr calculates changes in the concentration of $HbO_2$ and Hb in a blood flow from initial values, for example, by solving simultaneous equations using the light intensity of the internal scattering component I2 caused by the light from the light source Ls1 and the light intensity of the internal scattering component I2 caused by the light from the light source Ls2. Brain activity can be estimated on the basis of the obtained changes.

The arithmetic circuit Pr can be achieved, for example, by a DSP, a PLD such as an FPGA, or a combination of a CPU or a GPU and a computer program. The arithmetic circuit Pr and the control circuit Sy may be integrated as a single circuit.

The imaging apparatus D2 may include, between the image sensor S and the measurement target O, a bandpass filter that passes light having the wavelengths of the light emitted from the light sources Ls1 and Ls2.

The control circuit Sy determines a difference between a timing at which the light source Ls1 emits light and the shutter timing of the image sensor S and a difference between a timing at which the light source Ls2 emits light and the shutter timing of the image sensor S by the method described in the second embodiment. The control circuit Sy may adjust the timing(s) at which the light source Ls1 and/or the light source Ls2 emit light, or may adjust the shutter timing of the image sensor S.

Optical paths of the light that has been emitted from the light sources Ls1 and Ls2, reflected from the measurement target O, and has reached the image sensor S may be the same. A distance between the image sensor S and the light source Ls1 and a distance between the image sensor S and the light source Ls2, therefore, may be the same. The light sources Ls1 and Ls2, for example, may be arranged at rotationally symmetrical positions around the image sensor S.

The imaging apparatus D2 may include two images sensors S, instead. In this case, a bandpass filter that selectively passes light having the wavelength of the light emitted from the light source Ls1 may be provided in front of one of the image sensors S. In addition, a bandpass filter that selectively passes light having the wavelength of the light emitted from the light source Ls2 may be provided in front of the other image sensor S. In this case, the light sources Ls1 and Ls2 may emit light at the same time, and images can be captured simultaneously using the two image sensors S. If the imaging apparatus D2 includes only one image sensor S, images of two wavelengths can be obtained by capturing an image using the light source Ls1 and capturing an image using the light source Ls2 at different times.

In the case of a measurement target O that indicates more complex spectral characteristics, the measurement target O can be analyzed more accurately by increasing the number of wavelengths. As an imaging method in which the number of wavelengths is larger, a method in which the number of light sources is increased in accordance with the number of wavelengths or another known method may be used.

Fourth Embodiment

In a fourth embodiment, an example will be described in which an image of a person's head is captured using one of the imaging apparatuses according to the first to third embodiments. Detailed description of features common to the present embodiment and the first to third embodiments is omitted herein.

Figure 6A:
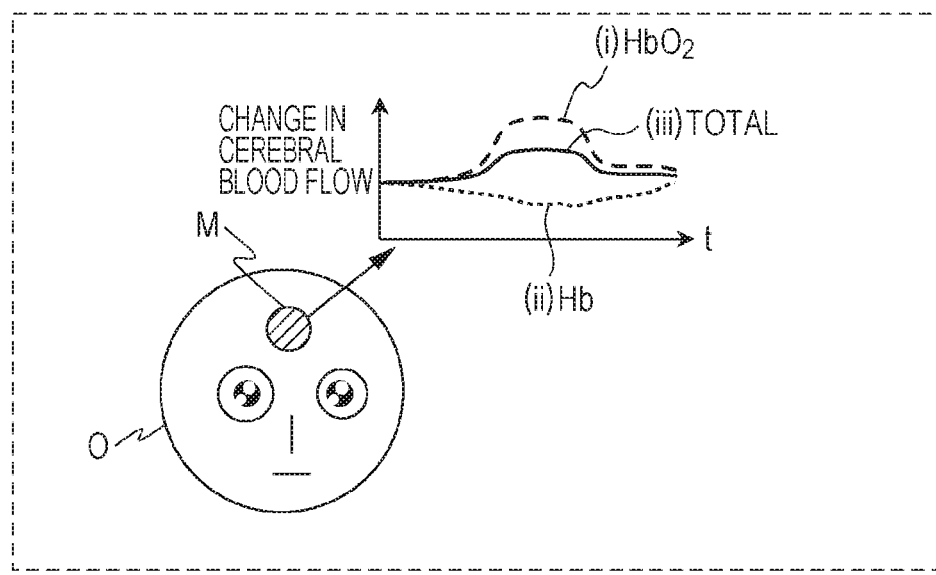
FIG. 6A is a diagram illustrating an example of measurement of changes in brain activity according to a fourth embodiment using an imaging apparatus in the present disclosure.

FIG. 6A illustrates an example in which changes in brain activity are measured using the imaging apparatus D2 according to the third embodiment (includes the two light sources Ls1 and Ls2). FIG. 6A is a diagram illustrating a detection area M in which the internal scattering component I2 is detected, (i) the amount of change in the concentration of $HbO_2$ in a blood flow from an initial value measured in the detection area M, (ii) the amount of change in the concentration of Hb in the blood flow from an initial value measured in the detection area M, and (iii) temporal changes in the sum of the amount of change in the concentration of $HbO_2$ in the blood flow and the amount of change in the concentration of Hb in the blood flow. If a brain activity state of the measurement target O changes over time between a normal state, a concentrated state, a relaxed state, and the like, the changes cause the temporal changes indicated by (i) to (iii). While (i) to (iii) are being measured, the detection area M may remain at the same position as precisely as possible. This is because the brain activity and the absorption and scattering coefficients are different between areas of the brain. When temporal changes in the brain activity are observed, an emotional state of the measurement target O can be estimated on the basis of temporal changes in absorbance (or the amount of light that has particular wavelengths and reaches the image sensor S without being absorbed) even if absolute magnitudes or true values of the concentration of $HbO_2$ and Hb in the blood flow are unknown. In addition, two wavelength bands need not necessarily be used for detecting temporal changes in the brain activity. Only one wavelength band may be used, instead. That is, an imaging apparatus such as that according to the first embodiment, which includes only one light source Ls, may be used. In this case, the light source Ls is preferably configured to emit light of a wavelength of 810 to 880 nm. This is because the absorbance of $HbO_2$ usually changes more largely than that of Hb when the brain activity changes, and patterns of changes in the brain activity can be found just by measuring a wavelength range in which the absorbance of $HbO_2$ is high.

Figure 6B:
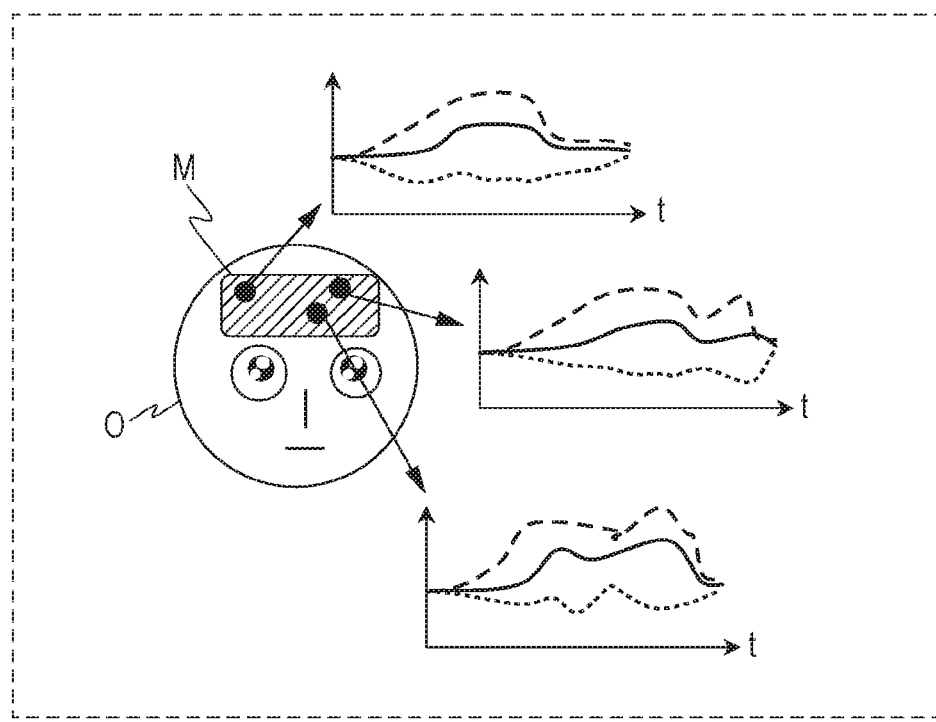
FIG. 6B is a diagram illustrating another example of the measurement of changes in brain activity according to the fourth embodiment using the imaging apparatus in the present disclosure.

FIG. 6B illustrates an example in which measurement is simultaneously performed at a plurality of points in the detection area M. An emission pattern of the light source Ls, for example, may have a uniform intensity distribution, a dotted intensity distribution, or a donut-shaped intensity distribution in the detection area M. If light of a uniform intensity distribution is emitted, adjustment of emission positions on the measurement target O need not be performed or can be simplified. In addition, since light enters the measurement target O from various angles, the strength of a signal detected by the image sensor S can be increased. Furthermore, measurement can be performed at arbitrary spatial positions within the emission area. In the case of partial emission such as a dotted intensity distribution or a donut-shaped intensity distribution, an effect of the surface reflection component I1 can be reduced just by removing the detection area M from the emission area. In this case, for example, the image sensor S may determine whether each pixel in a captured image falls within the emission area. An area including pixels determined to fall within non-emission areas may then be determined as a detection area, and measurement for detecting the internal scattering component I2 may be performed. The determination whether each pixel falls within the emission area may be made on the basis of whether the luminance of each pixel is larger than a certain threshold. Since the intensity of surface reflection component I1 and that of the internal scattering component I2 are largely different from each other, it becomes difficult to measure the internal scattering component I2 if the emission area, however small, remains in the detection area M. The present method can therefore be effectively used.

Figure 7A:
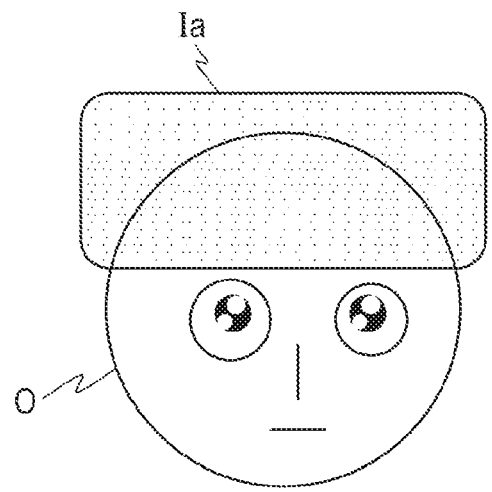
FIG. 7A is a diagram illustrating an emission area of light.
Figure 7B:
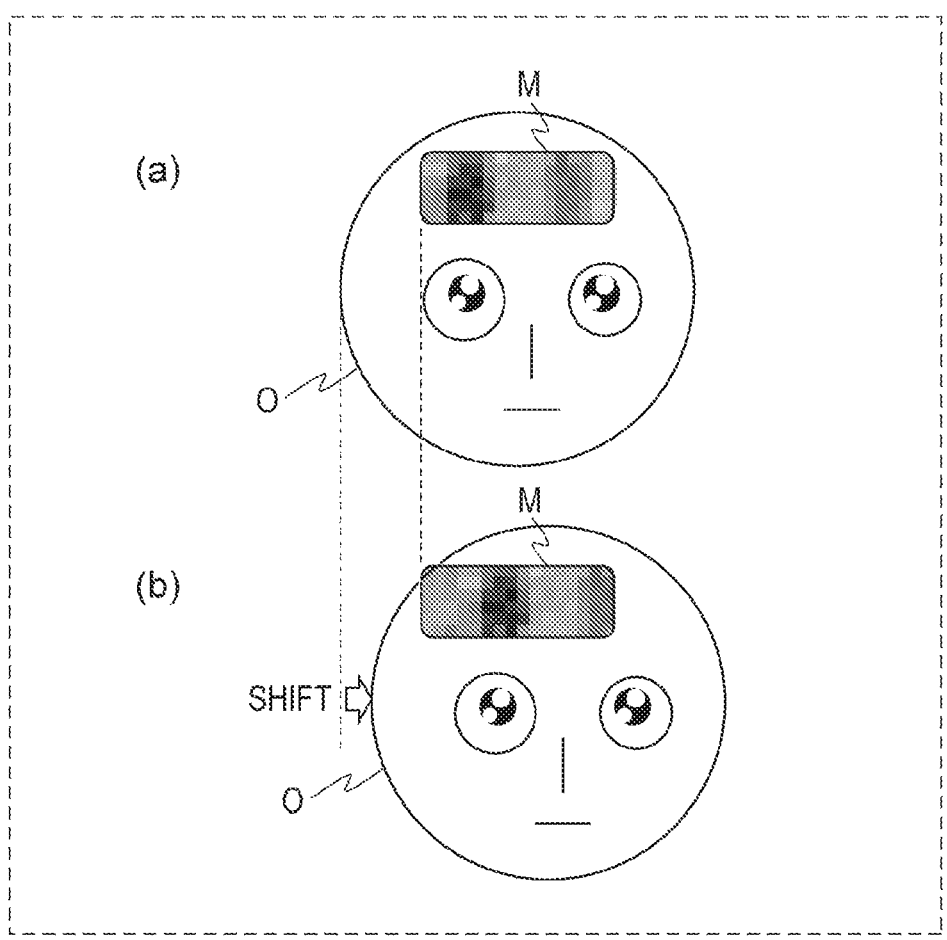
FIG. 7B is a diagram illustrating a two-dimensional brain activity distribution in a detection area.

FIG. 7A illustrates an emission area Ia of the light source Ls, and FIG. 7B illustrates a two-dimensional distribution of brain activity in the detection area M. If a cerebral blood flow is measured in a noncontact manner, the amount of light detected undesirably attenuates in accordance with a square of the distance between the measurement target O and the image sensor S. A signal of each pixel detected by the image sensor S may be complemented by nearby pixels and strengthened. In doing so, the number of pulses of light emitted from the light source Ls can be decreased while maintaining the S/N ratio, and the frame rate improves. In measurement of a cerebral blood flow, a change caused by a brain activity in a normal state is measured in order to read a change in brain activity. Since the image sensor S including the pixels arranged in two dimensions is used in the present disclosure, a two-dimensional distribution of brain activity can be obtained as illustrated in FIG. 7B. A portion of a brain that is highly active can be detected on the basis of a relative intensity distribution even if the normal state is obtained in advance.

A state in which the detection area M of the image sensor S has changed during measurement as a result of movement of the measurement target O due to breathing or the like is illustrated in (b) of FIG. 7B. Because, in general, brain activity distribution does not sharply changes in a short period of time, the shift of the detection area M can be corrected through, for example, pattern matching between frames of the detected two-dimensional distribution. Alternatively, in the case of periodical movement caused by breathing or the like, only corresponding frequency components may be extracted and corrected or removed.

Fifth Embodiment

A fifth embodiment illustrates an example in which one of the imaging apparatuses according to the first to third embodiments is used. Detailed description of features common to the present embodiment and the first to third embodiments is omitted herein.

Figure 8A:
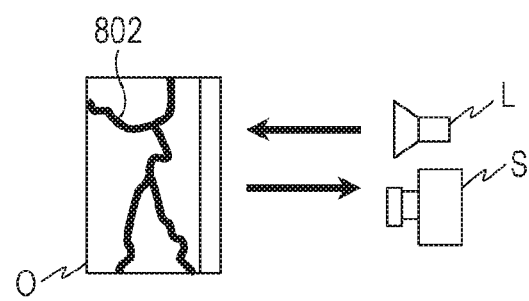
FIG. 8A is a diagram illustrating an example in which a material analysis and a structure analysis are performed on an inside of the measurement target according to a fifth embodiment using the imaging apparatus in the present disclosure.
Figure 8B:
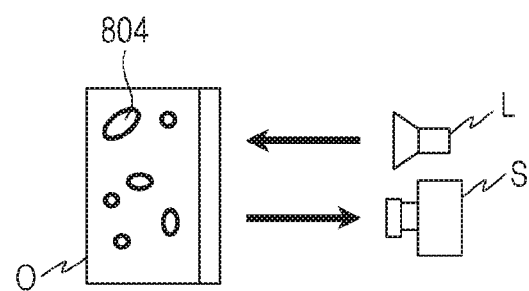
FIG. 8B is a diagram illustrating another example in which a material analysis and a structure analysis are performed on the inside of the measurement target according to the fifth embodiment using the imaging apparatus in the present disclosure.

In the fifth embodiment, an internal structure of the measurement target O is diagnosed. In order to diagnose the internal structure of the measurement target O, the effect of the surface reflection component I1 is suppressed. In the fifth embodiment, one of the imaging apparatuses according to the first to third embodiments is used to diagnose the internal structure of the measurement target O. As illustrated in FIGS. 8A and 8B, if there is a deterioration or a structural change inside the measurement target O, such as cracks 802 or cavities 804, the optical path of the internal scattering component I2 changes because of a change in an index of refraction or interface reflection. If the optical path of the internal scattering component I2 changes, a time at which the internal scattering component I2 reaches the image sensor S and the coherence of light change. In the fifth embodiment, a deterioration in the measurement target O or a processing state of the measurement target O is checked by detecting these changes.

Figure 9A:
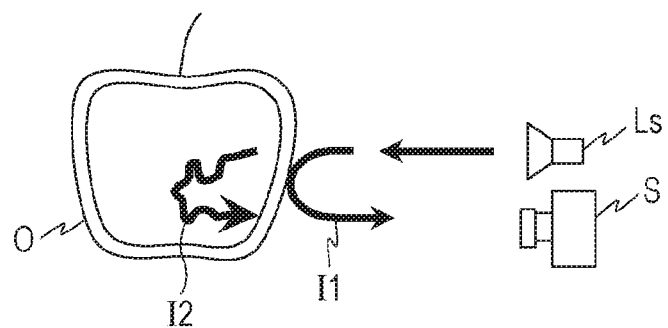
FIG. 9A is a diagram illustrating an example in which a material analysis and a structure analysis are performed on the inside of the measurement target by separating an internal scattering component from a surface reflection component in light reflected from the measurement target according to the fifth embodiment using the imaging apparatus in the present disclosure.
Figure 9B:
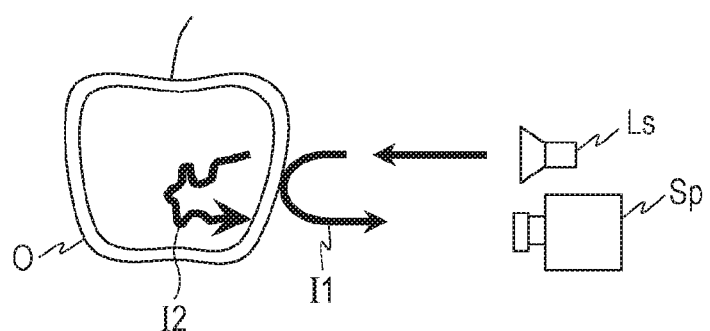
FIG. 9B is a diagram illustrating an example in which a material analysis and a structure analysis are performed on the inside of the measurement target by obtaining multi-wavelength information regarding the internal scattering component according to the fifth embodiment using the imaging apparatus in the present disclosure.

FIG. 9A illustrates an example in which information regarding an inside of a fruit is obtained using one of the imaging apparatuses according to the first to third embodiments. In an example of the related art, the fruit needs to be peeled before measurement in order to eliminate an effect of skin. The inside of the fruit, however, can be inspected in a nondestructive manner using one of the imaging apparatuses according to the first to third embodiments while eliminating information regarding the skin. In FIG. 9B, the image sensor S further includes a multi-wavelength detector Sp. The multi-wavelength detector Sp is a camera that obtains a multi-wavelength image. A camera in which a filter that passes a different wavelength is provided for each pixel or a camera that includes liquid crystal tunable filter or an acousto-optic device, for example, may be used as the multi-wavelength detector Sp. The "multi-wavelength", for example, refers to four to 100 wavelengths. Alternatively, a compressive sensing camera that generates an image (multi-wavelength information) for each of a multiple of wavelengths by performing a statistical operation on superimposed coded multi-wavelength information and reconstructing original multi-wavelength information. By obtaining the multi-wavelength information, the sugar content, maturity, and deterioration of the measurement target O can be measured.

Sixth Embodiment

A sixth embodiment is different from the first to third embodiments in that the internal scattering component I2 of the measurement target O is resolved for each optical length. Detailed description of features common to the present embodiment and the first to third embodiments is omitted herein.

Figure 10:
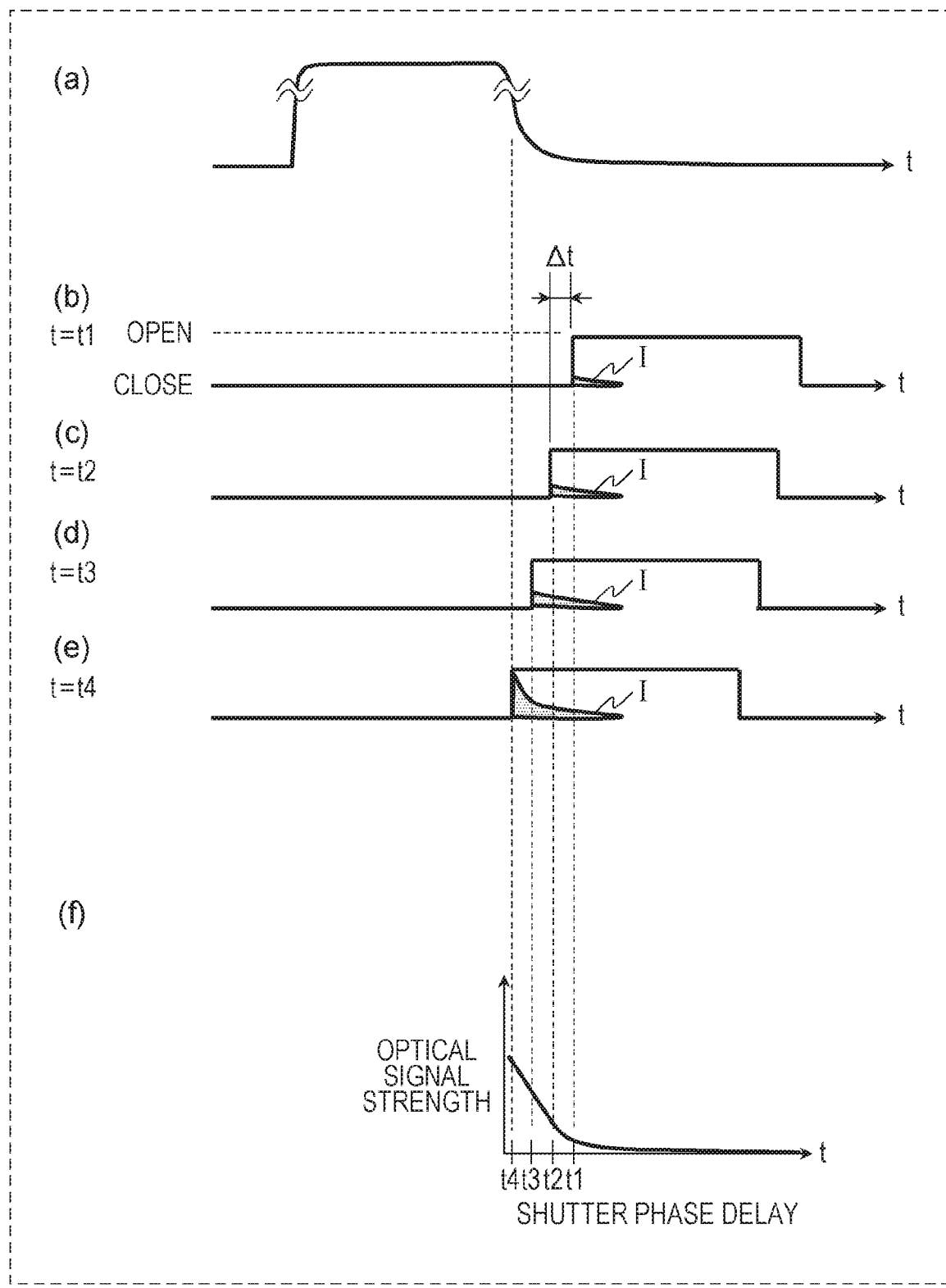
FIG. 10 is a diagram illustrating the configuration of time resolution of the internal scattering component according to a sixth embodiment.

A time response waveform of an optical signal that reaches the image sensor S is illustrated in (a) of FIG. 10. If the pulse width of the light source Ls is small enough, it can be regarded that an optical length distribution is illustrated in (a) of FIG. 10. That is, since light having a long optical path reaches the image sensor S late, the time t at which the light is detected is large (late). That is, the time response waveform has an extension according to the optical length distribution.

Shutter timings with the phase t=t, t2, t3, and t4, respectively (t1>t2>t3>t4) are illustrated in (b) to (e) of FIG. 10. The "phase" refers to a difference between the timing at which the light source Ls emits pulsed light and the shutter timing of the image sensor S. A diagram in which a horizontal axis represents the phases of the shutter timings illustrated in (b) to (e) of FIG. 10 and a vertical axis represents the strength of a signal I detected by a target pixel at each shutter timing is illustrated in (f) of FIG. 10. The detected signal I includes light having a relatively long optical path when t=t1, which is a latest time, and includes light having a relatively short optical path when t=t4, which an earliest time. An optical length distribution corresponding to a trailing edge of the optical signal illustrated in (a) of FIG. 10 can be obtained, for example, by differentiating the graph (f) of FIG. 10 or obtaining differences between detected signals I for each phase difference. Because the optical length distribution relates to length information regarding an inside of the measurement target O, depth information regarding the measurement target O can be estimated.

The phase may be changed by changing the shutter timing or by changing the timing at which the light source Ls emits pulsed light.

If the pulse width of the light source Ls is large, the pulsed light of the light source Ls can be regarded as a series of pulsed light beams having short pulse widths. The optical signal illustrated in (a) of FIG. 10, therefore, is convolution of detected signals caused by the pulsed light beams having short pulse widths. A desired optical length distribution can be obtained, therefore, by differentiating a derivative of the graph of FIG. 10(f) (that is, by obtaining a second derivative).

As described above, the control circuit Sy detects a time-resolved signal at a time at which a trailing edge of pulsed light reflected from the surface of the measurement target O reaches the image sensor S or later. More specifically, the control circuit Sy captures a plurality of images with varying phases. An optical length distribution of the internal scattering component I2 can be obtained on the basis of changes in signal strength obtained from the plurality of images.

Seventh Embodiment

In a seventh embodiment, an example will be described in which an internal scattering component I2 distant from the surface of the measurement target O is detected using one of the imaging apparatuses according to the first to third embodiments. Detailed description of the same features as in the first to third embodiment is omitted.

Figure 11:
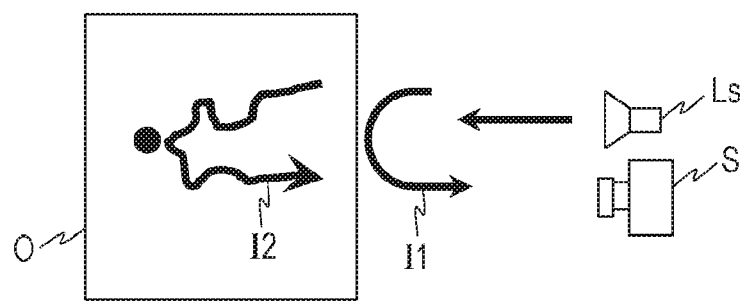
FIG. 11 is a diagram illustrating a configuration according to a seventh embodiment by which the internal scattering component that has reached a position relatively distant from a surface of the measurement target is detected.

FIG. 11 is a diagram illustrating an imaging apparatus that detects a relatively large amount of the internal scattering component I2 distant from the surface of the measurement target O among components scattered inside the measurement target O. The internal scattering component I2 distant from the surface of the measurement target O can be obtained by making the shutter timing of the image sensor S later than a trailing edge of the surface reflection component I1. In the case of a shutter timing with which the surface reflection component I1 is not included, the shutter width may be sufficiently larger than the pulse width of emitted pulsed light. The shutter width, for example, may be five, 10, or 100 times as large as the pulse width.

First Example

Figure 12:
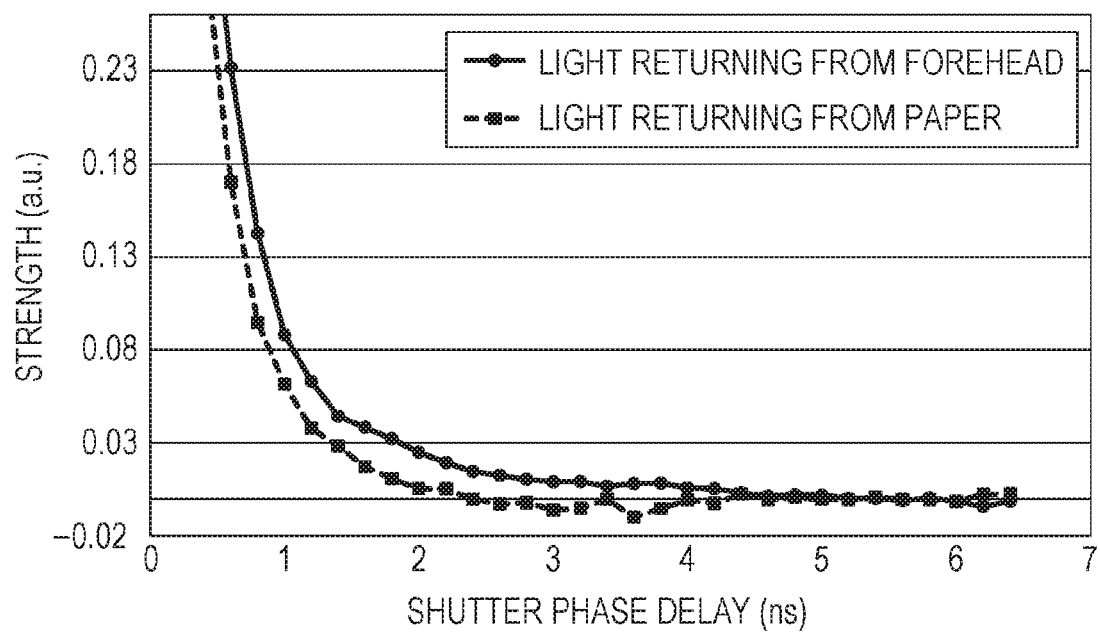
FIG. 12 is a diagram illustrating a result of measurement in a first example.

An example in which an image of a person's forehead was captured as the measurement target O will be described. In FIG. 12, a horizontal axis represents a difference between the shutter timing and the timing at which the light source Ls emits pulsed light, that is, a phase delay, and a vertical axis represents the strength of an optical signal I from the image sensor S obtained from an image captured at the shutter timing. During a process for capturing images, the shutter timing was changed in steps of 200 ps. The detection area M in which optical signals I were detected includes 50×50 pixels. The wavelength of light emitted from the light source Ls was 850 nm. A distance between the forehead and the light source Ls (image sensor S) was 10 cm. A sheet of paper that blocks near-infrared light covered part of the forehead, and measurement was performed on both the forehead and the sheet of paper. FIG. 12 illustrates light returning from the forehead and light returning from the sheet of paper. Values along the vertical axis illustrated in FIG. 12 are values normalized with pixel values separately obtained by capturing images of the forehead and the sheet of paper using the entirety of pulsed light such that saturation does not occur. In FIG. 12, a part around a phase delay of 1 ns in which strength sharply drops corresponds to a trailing edge of pulsed light. As illustrated in FIG. 12, in a part later than the trailing edge of the pulsed light, the light returning from the forehead is more intense than the light returning from the pieces of paper. That is, the light returning from the forehead includes the internal scattering component I2 at times later than the trailing edge of the pulsed light. It can thus be seen that only information regarding the person's brain can be detected in a noncontact manner.

Figure 13:
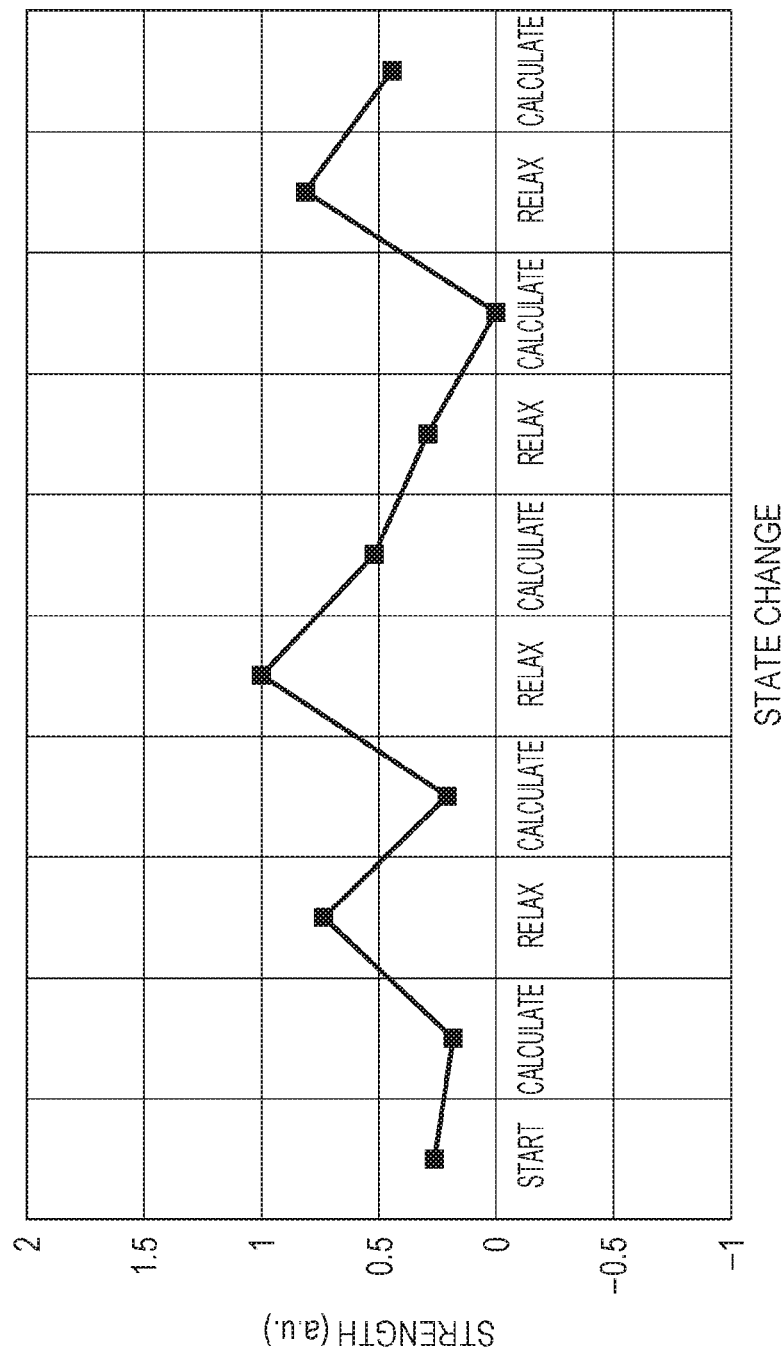
FIG. 13 is a diagram illustrating a result of measurement of changes in brain activity in the first example.

FIG. 13 illustrates a result of capture of images of the forehead at a shutter timing fixed at a phase delay of 4 ns. During the image capture, a subject alternately entered a relaxed state and a concentrated state (calculation) at intervals of 30 seconds. Measurement was performed at intervals of 30 seconds, and results of the measurement were normalized with maximum and minimum values. In FIG. 13, the strength of detected light signals during calculation are lower than in the relaxed state. This can be because the light of a wavelength of 850 nm is absorbed more by $HbO_2$ than by Hb, and $HbO_2$ that had increased during calculation absorbed the light.

What is claimed is:

1. An imaging apparatus comprising:
   a light source that emits a light pulse to a target;
   an image sensor that detects a returned light pulse which is returned from the target to the image sensor due to emission of the light pulse; and
   a circuit that controls the image sensor,
   wherein the circuit
   causes the image sensor to start detecting a component of the returned light pulse at a timing in a falling period of the returned light pulse, the falling period being from a beginning to an end of a period in which an intensity of the returned light pulse decreases, and
   generates multi-wavelength images based on the component of the returned light pulse detected by the image sensor.

2. The imaging apparatus according to claim 1, wherein the circuit
   causes the image sensor to obtain superimposed multi-wavelength information based on the component of the returned light pulse; and
   generating the multi-wavelength images by performing a reconstruction operation on the superimposed multi-wavelength information.

3. The imaging apparatus according to claim 1, wherein the multi-wavelength images include images for each of a multiple of wavelengths.

4. The imaging apparatus according to claim 1, wherein the circuit evaluates at least one selected from the group consisting of sugar content, maturity, and deterioration of the target.

5. The imaging apparatus according to claim 1, wherein the image sensor includes pixels arranged in two dimensions.

6. The imaging apparatus according to claim 1, wherein the image sensor includes at least one pixel, the at least one pixel including a photodiode and charge accumulators that accumulate signal charge from the photodiode.

7. The imaging apparatus according to claim 1, further comprising a correction circuit that corrects movement of the target.

8. The imaging apparatus according to claim 7, wherein the correction circuit corrects the movement of the target by detecting periodic vibration of the target.

9. The imaging apparatus according to claim 1, wherein the multi-wavelength images are images denoting an inside of the target.

10. The imaging apparatus according to claim 1, wherein the component of the returned light pulse is an internal scattering component that corresponds to a light that passes through the target and exits from a surface of the target in response to the light source emitting the light pulse to the surface of the target.

11. The imaging apparatus according to claim 1,
wherein the multi-wavelength images include at least four images, and
wherein each of the at least four images is an image for a corresponding one of at least four wavelength bands.

* * * * *